United States Patent
O'Neil et al.

(10) Patent No.: US 8,901,071 B2
(45) Date of Patent: Dec. 2, 2014

(54) COMPOUNDS AND THEIR USE

(75) Inventors: Deborah O'Neil, Aberdeen (GB); Derry Mercer, Aberdeen (GB); Cedric Charrier, Aberdeen (GB)

(73) Assignee: Novabiotics Limited, Aberdeen (GB)

(*) Notice: Subject to any disclaimer, the term of this patent is extended or adjusted under 35 U.S.C. 154(b) by 0 days.

(21) Appl. No.: 13/638,436

(22) PCT Filed: Mar. 30, 2011

(86) PCT No.: PCT/GB2011/000480
§ 371 (c)(1),
(2), (4) Date: Dec. 17, 2012

(87) PCT Pub. No.: WO2011/121289
PCT Pub. Date: Oct. 6, 2011

(65) Prior Publication Data
US 2013/0102524 A1    Apr. 25, 2013

Related U.S. Application Data

(60) Provisional application No. 61/390,081, filed on Oct. 5, 2010.

(30) Foreign Application Priority Data

Mar. 31, 2010  (WO) ............... PCT/GB2010/000631
Oct. 5, 2010   (GB) .................................. 1016733.6

(51) Int. Cl.
| | | |
|---|---|---|
| *C07K 7/08* | (2006.01) | |
| *A61K 38/08* | (2006.01) | |
| *A61K 38/17* | (2006.01) | |
| *A61K 38/10* | (2006.01) | |
| *A61K 9/08* | (2006.01) | |
| *A61K 38/00* | (2006.01) | |
| *A61K 45/06* | (2006.01) | |
| *A61K 31/145* | (2006.01) | |

(52) U.S. Cl.
CPC . *C07K 7/08* (2013.01); *A61K 38/10* (2013.01); *A61K 38/08* (2013.01); *A61K 45/06* (2013.01); *A61K 31/145* (2013.01)
USPC .............................. 514/2.7; 514/2.8; 530/327

(58) Field of Classification Search
CPC ........ C07K 7/06; C07K 7/08; C07K 14/4723; C07K 5/08; C07K 5/10; A61K 38/08; A61K 38/10; A61K 38/1729; A61K 38/06; A61K 38/07; A61K 2300/00; A61K 31/145; A61K 45/06; A61K 9/08
USPC ....................................................... 530/327
See application file for complete search history.

(56) References Cited

FOREIGN PATENT DOCUMENTS

| EP | 2168590 A1 | 3/2010 |
|---|---|---|
| GB | 2408263 A | 5/2005 |
| WO | WO 2008/093058 A2 | 8/2008 |

OTHER PUBLICATIONS

Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
K. Weller, Biophysical and Biological Studies on End Group Modified Derivatives of Pep-1, Biochemistry, 2005, 44, 15799-15811.*
Chen, Po-Wen, et al., "Antibacterial Activity of Short Hydrophobic and Basic-Rich Peptides," Amer. J. of Vet. Res., vol. 64, No. 9, p. 1088-1092, Sep. 2003.
Jayaraman, A. et al., "Inhibiting Sulfate-Reducing Bacteria in Biofilms by Expressing of Antimicrobial Reptides Indolicidin and Bactenecin," J. of Industrial Microbiol. and Biotechn. vol. 22, p. 167-175, Jan. 1, 1999.

* cited by examiner

*Primary Examiner* — Julie Ha
*Assistant Examiner* — Erinne Dabkowski
(74) *Attorney, Agent, or Firm* — Morgan, Lewis & Bockius LLP

(57) ABSTRACT

The present invention relates to peptides and their use in the treatment of microbial infections, in particular bacterial infections. In particular, the invention relates to peptides wherein at least 75% of the amino acids of the peptide are arginine and phenylalanine amino acids, at least 50% of the amino acids being arginine amino acids and at least 15% of the amino acids being phenylalanine amino acids.

14 Claims, 12 Drawing Sheets

Figure 5:
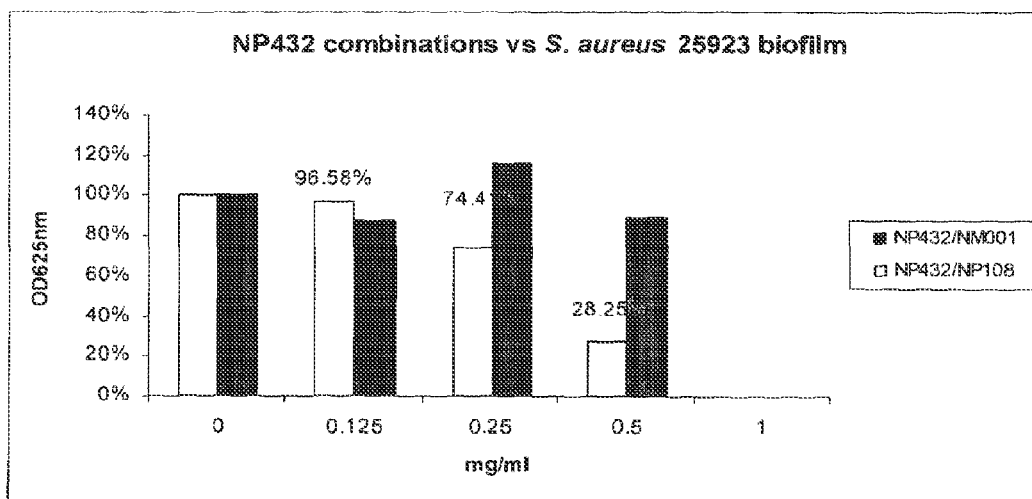

| | NP | Sequence | S. epidermidis ATCC12228 | | | S. aureus ATCC29323 | | | S. aureus DSMZ11729 | | | C. difficile NCTC11209 | | | E. faecium ATCC19434 | | | E. faecalis ATCC29212 | | | S. aureus PLC64 (MRSA) | | |
|---|---|---|---|---|---|---|---|---|---|---|---|---|---|---|---|---|---|---|---|---|---|---|
| | | | MIC100 | MIC90 | MIC50 | MIC100 | MIC90 | MIC50 | MIC100 | MIC90 | MIC50 | MIC100 | MIC90 | MIC50 | MIC100 | MIC90 | MIC50 | MIC100 | MIC90 | MIC50 | MIC100 | MIC90 | MIC50 |
| SEQ ID No.1 | NP432 | RRRRFRFFRFRRR | 4 | 4 | 2 | 31.25 | 31.25 | <7.8 | 62.5 | 62.5 | <7.8 | | | | | | | | | | | | |
| SEQ ID No.2 | NP438 | HHHFHFFFFHRRR | <7.8 | <7.8 | 7.9 | >500 | >500 | 250 | >500 | >500 | 125 | | | | | | | | | | | | |
| SEQ ID No.3 | NP446 | KKFPWKLPLRYGRR | 31.25 | 31.25 | <7.8 | 500 | 500 | 125 | 500 | 500 | 125 | | | | | | | | | | | | |
| SEQ ID No.4 | NP455 | RRRRHFFFRFRR | <7.8 | <7.8 | <7.8 | 31.25 | 31.25 | 31.25 | 125 | 125 | 62.5 | | | | | | | | | | | | |
| SEQ ID No.5 | NP456 | RRRRFRFRFRRR | <7.8 | <7.8 | <7.8 | 15.6 | 15.6 | 7.8 | 125 | 125 | 7.8 | | | | | | | | | | | | |
| SEQ ID No.6 | NP467 | RRRFFFPFRRR | <7.8 | <7.8 | <7.8 | 62.5 | 62.5 | 31.25 | 125 | 125 | 62.5 | | | | | | | | | | | | |
| SEQ ID No.7 | NP468 | RRRRFFFRRR | 15.6 | 15.6 | 7.8 | 62.5 | 62.5 | 15.6 | 125 | 125 | 62.5 | | | | | | | | | | | | |
| SEQ ID No.8 | NP469 | RRRRFFFRRR | 15.6 | 15.6 | 15.6 | 500 | 500 | 125 | 500 | 500 | 250 | | | | | | | | | | | | |
| SEQ ID No.9 | NP470 | RRRFFFRRRR | 125 | 125 | 31.25 | 500 | 500 | 250 | 500 | 500 | 62.5 | | | | | | | | | | | | |
| SEQ ID No.10 | NP471 | RRRRFFFFRRR | 62.5 | 62.5 | 31.25 | 500 | 500 | 250 | >500 | >500 | 125 | | | | | | | | | | | | |
| SEQ ID No.11 | NP472 | RRFRRRFFFRRR | 31.25 | 31.25 | 15.6 | 250 | 250 | 125 | 500 | 500 | 125 | | | | | | | | | | | | |
| SEQ ID No.12 | NP473 | RRFRFRFFFRFG | 125 | 125 | 31.25 | 500 | 500 | 250 | 500 | 500 | 500 | | | | | | | | | | | | |
| SEQ ID No.13 | NP474 | RRFGRRFRRFFG | 125 | 125 | 31.25 | 500 | 500 | 500 | 500 | 500 | 500 | | | | | | | | | | | | |
| SEQ ID No.14 | NP475 | RRFRFRFRRFG | 125 | 125 | 31.25 | 500 | 500 | 500 | 500 | 500 | 125 | | | | | | | | | | | | |
| SEQ ID No.15 | NP476 | RRFRFRFFFFRR | 62.5 | 62.5 | 15.6 | 500 | 500 | 250 | 500 | 500 | 250 | | | | | | | | | | | | |
| SEQ ID No.16 | NP480 | FRRRRFFFFHRRR | | | | 31.25 | 31.25 | 15.625 | 62.5 | 62.5 | 7.8 | | | | | | | | | | | | |
| SEQ ID No.17 | NP491 | HHHRFFFFFRRRF | | | | 125 | 125 | 62.5 | 250 | 125 | 31.25 | | | | | | | | | | | | |
| SEQ ID No.18 | NP492 | FFFFRRRRRRRR | | | | 62.5 | 15.625 | 7.8 | 125 | 62.5 | 7.8 | | | | | | | | | | | | |
| SEQ ID No.19 | NP493 | RRRRFFFFRRRR | | | | 250 | 31.25 | 15.625 | 31.25 | 31.25 | 7.8 | | | | | | | | | | | | |
| SEQ ID No.20 | NP494 | RRRFFFRRRRF | | | | 125 | 62.5 | 31.25 | 125 | 125 | 31.25 | | | | | | | | | | | | |
| SEQ ID No.21 | NP495 | RRRYRYYYRYRRR | | | | 250 | 250 | 125 | 250 | 250 | 250 | | | | | | | | | | | | |
| SEQ ID No.22 | NP496 | RRRARAAARRRR | | | | 500 | 500 | 500 | 500 | 500 | 250 | | | | | | | | | | | | |
| SEQ ID No.23 | NP497 | RRRFRRRRFFFF | | | | 31.25 | 15.625 | 15.625 | 31.25 | 31.25 | 31.25 | | | | | | | | | | | | |
| SEQ ID No.24 | NP498 | RRRFFFFFRRR | 15.6 | 15.8 | 7.8 | >500 | >500 | 500 | >500 | >500 | 125 | | | | | | | | | | | | |
| | NP432C | RRRFRFFRFRRR-Cysteamine | 500 | 500 | 250 | 500 | 500 | 500 | 500 | 500 | 500 | | | | | | | | | | | | |
| | NM001 | Cysteamine | | | | | | | | | | 1000 | 1000 | 1000 | | | | | | | 512 | 512 | 512 |

Figure 1

Figure 1a

| SEQ ID No. | NP | Sequence | P. aeruginosa DSM21135 | | | P. aeruginosa DSM21289 | | | P. aeruginosa ATCC BAA-47 | | | P. aeruginosa 5728SA | | | P. aeruginosa 6728SB | | | P. aeruginosa 6738SC | | | P. aeruginosa 6734SD | | | P. aeruginosa 50071 | | | P. aeruginosa PA14 | | | P. aeruginosa PA058 | | |
|---|---|---|---|---|---|---|---|---|---|---|---|---|---|---|---|---|---|---|---|---|---|---|---|---|---|---|---|---|---|---|---|---|
| | | | MIC 100 | MI C9 | MI C5 | MIC 100 | MI C9 | MI C5 | MIC 100 | MI C9 | MI C5 | MIC 100 | MI C9 | MI C5 | MIC 100 | MI C9 | MI C5 | MIC 100 | MI C9 | MI C5 | MIC 100 | MI C9 | MI C5 | MIC 100 | MI C9 | MI C5 | MIC 100 | MI C9 | MI C5 | MIC 100 | MI C9 | MI C5 |
| 1 | NP432 | RRRFRRFFFR FRRR | 62.5 | 46.9 | 15.6 | 15.6 | 15.6 | 15.6 | 15.6 | 15.6 | 15.6 | 31.25 | 31.25 | 31.25 | 15.6 | 15.6 | 15.6 | 31.25 | 31.25 | 19.5 | 62.5 | 62.5 | 31.25 | 15.6 | 15.6 | 7.8 | 15.6 | 15.6 | 7.8 |
| 2 | NP433 | HHHFRRFFR FRRR | >50 0 | >50 0 | 500 | 500 | >50 0 | >50 0 | >50 0 | 500 | 500 | | | | | | | | | | | | | | | | | | |
| 3 | NP465 | RAFPVRLRL RYGRR | 62.5 | 62.5 | 62.5 | 31.25 | 31.25 | 31.25 | 31.25 | 31.25 | 31.25 | | | | | | | | | | | | | | | | | | |
| 4 | NP466 | RRRRFRFFR RRRR | 125 | 125 | 125 | 31.25 | 31.25 | 31.25 | 125 | 125 | 62.5 | 62.5 | 62.5 | 31.25 | 125 | 125 | 31.25 | 62.5 | 62.5 | 31.25 | | | | | | | | | |
| 5 | NP466 | RRRFRRFFR FRRR | 500 | 500 | 7.8 | 15.6 | 15.6 | 15.6 | 125 | 125 | 7.8 | 62.5 | 62.5 | 31.25 | 62.5 | 62.5 | 15.6 | 62.5 | 62.5 | 7.8 | | | | | | | | | |
| 6 | NP467 | RRRFRFFR FRRR | 500 | 500 | 125 | 125 | 125 | 125 | 250 | 250 | 62.5 | 250 | 250 | 62.5 | 125 | 125 | 62.5 | 125 | 125 | 31.25 | | | | | | | | | |
| 7 | NP468 | RRRFRFFFR RFRR | 500 | 500 | 125 | 62.5 | 62.5 | 62.5 | 250 | 250 | 31.25 | 250 | 250 | 31.25 | 250 | 250 | 31.25 | 125 | 125 | 31.25 | | | | | | | | | |
| 8 | NP469 | RRRRFFFR RR | | | | | | | 250 | 250 | 125 | 125 | 125 | 125 | 250 | 250 | 125 | 125 | 125 | 31.25 | | | | | | | | | |
| 9 | NP470 | RRRRFFFR RRR | | | | | | | 250 | 250 | 250 | | | | | | | | | | | | | | | | | | |
| 10 | NP471 | RRRRFFFR FR | | | | | | | 500 | 500 | 500 | | | | | | | | | | | | | | | | | | |
| 11 | NP472 | RRFFRRRFR RFH | | | | | | | 500 | 500 | 250 | | | | | | | | | | | | | | | | | | |
| 12 | NP473 | RRRFRRFFR RFG | | | | | | | 500 | 500 | 250 | | | | | | | | | | | | | | | | | | |
| 13 | NP474 | RRFSFFRR RFG | | | | | | | 500 | 500 | 500 | | | | | | | | | | | | | | | | | | |
| 14 | NP475 | RRFRRFFFR RFR | | | | | | | 500 | 500 | 125 | | | | | | | | | | | | | | | | | | |
| 15 | NP479 | RFRRFFFR NFR | | | | | | | 125 | 125 | 125 | | | | | | | | | | | | | | | | | | |
| 16 | NP480 | RRRFRRFFR FRRR | 62.5 | 62.5 | 15.6 | 125 | 125 | 31.25 | 31.25 | 31.25 | 31.25 | 31.25 | 31.25 | 15.6 | 31.25 | 31.25 | 15.6 | 62.5 | 62.5 | 31.25 | 15.6 | 15.6 | 7.8 | 15.6 | 15.6 | 7.8 | 31.25 | 31.25 | 7.8 |
| 17 | NP481 | RRRFRFFR FRRR | 250 | 250 | 62.5 | 250 | 250 | 125 | 250 | 250 | 62.5 | | | | | | | | | | | | | | | | | | |
| 18 | NP482 | RRFRRRFR RRPF | 500 | 500 | 250 | 250 | 250 | 125 | 500 | 500 | 500 | | | | | | | | | | | | | | | | | | |
| 19 | NP483 | FFFRRRRR FFRR | 125 | 125 | 15.6 | 31.25 | 31.25 | 15.6 | 15.6 | 15.6 | 15.6 | | | | | | | | | | | | | | | | | | |
| 20 | NP484 | RRRFRRFFR RRRH | 250 | 250 | 250 | 250 | 250 | 125 | >50 0 | >50 0 | 125 | | | | | | | | | | | | | | | | | | |
| 21 | NP485 | RFFRFRFR RRPF | >50 0 | >50 0 | >50 0 | >50 0 | >50 0 | >50 0 | 500 | 500 | 500 | | | | | | | | | | | | | | | | | | |
| 22 | NP486 | RRFVYYVV RYRR | >50 0 | >50 0 | >50 0 | >50 0 | >50 0 | >50 0 | >50 0 | >50 0 | >50 0 | | | | | | | | | | | | | | | | | | |
| 23 | NP487 | RRRAFAAA RARRR | 15.6 | 25 | 15.6 | 31.25 | 31.25 | 15.6 | 62.5 | 62.5 | 62.5 | 15.6 | 15.6 | 15.6 | 31.25 | 31.25 | 15.6 | 15.6 | 15.6 | 7.8 | | | | | | | | | |
| 24 | NP488 | RRRFRFFFR FRRR | 62.5 | 62.5 | 31.25 | 62.5 | 62.5 | 62.5 | 125 | 125 | 62.5 | | | | | | | | | | | | | | | | | | |
| | NP432C | RRRFRRFFR FRRR-Cysteamine | 250 | 250 | 250 | 250 | 250 | 250 | 250 | 250 | 250 | 250 | 250 | 250 | 250 | 250 | 250 | 250 | 250 | 7.8 | 500 | 500 | 250 | >25 0 | >25 0 | >25 0 | >25 0 | >25 0 | >25 0 |
| | RR001 | Cysteamine | | | | | | | | | | | | | | | | | | | | | | | | | | | |

Figure 1b

| SEQ ID NO. | NP | Sequence | B. cepacia NCTC10743 MIC100 | MIC90 | MIC50 | B. cepacia NCTC10744 MIC100 | MIC90 | MIC50 | A. baumannii NCTC12156 MIC100 | MIC90 | MIC50 | A. calcoaceticus NCTC7422 MIC100 | MIC90 | MIC50 | E. coli NCTC9434 MIC100 | MIC90 | MIC50 | E. coli NCTC1093 MIC100 | MIC90 | MIC50 | E. coli NCTC9001 MIC100 | MIC90 | MIC50 |
|---|---|---|---|---|---|---|---|---|---|---|---|---|---|---|---|---|---|---|---|---|---|---|---|
| 1 | NP432 | RRRFRFFRFRRR | >250 | >250 | 125 | >250 | >250 | >250 | 31.25 | 31.25 | 15.6 | 31.25 | 31.25 | 15.6 | 31.25 | 31.25 | 3.9 | 15.6 | 7.8 | 2 | 31.25 | 31.25 | 15.6 |
| 2 | NP438 | HHHFRFFRFRRR | | | | | | | | | | | | | | | | | | | | | |
| 3 | NP445 | KKFPWALRLRYGRK | | | | | | | | | | | | | | | | | | | | | |
| 4 | NP464 | RRRRFFFRFRRR | | | | | | | | | | | | | | | | | | | | | |
| 5 | NP466 | RRRRFRFFRKR | | | | | | | | | | | | | | | | | | | | | |
| 6 | NP467 | RRRFRFFRFRR | | | | | | | | | | | | | | | | | | | | | |
| 7 | NP468 | RRRFRFFRFRRR | | | | | | | | | | | | | | | | | | | | | |
| 8 | NP469 | RRRFFFFFRRR | | | | | | | | | | | | | | | | | | | | | |
| 9 | NP470 | RRRPFFRFRRR | | | | | | | | | | | | | | | | | | | | | |
| 10 | NP471 | RRRPFFKFRRR | | | | | | | | | | | | | | | | | | | | | |
| 11 | NP472 | RRRFFFRFRRR | | | | | | | | | | | | | | | | | | | | | |
| 12 | NP473 | RRRFRRFRRFG | | | | | | | | | | | | | | | | | | | | | |
| 13 | NP474 | RRFGRRFRRFG | | | | | | | | | | | | | | | | | | | | | |
| 14 | NP475 | RRFGRRFRRFG | | | | | | | | | | | | | | | | | | | | | |
| 15 | NP476 | RRRFRRFRRRR | | | | | | | | | | | | | | | | | | | | | |
| 16 | NP480 | RRRFRFFRFFFRRR | | | | | | | | | | | | | | | | | | | | | |
| 17 | NP491 | RRRRFRFFRRRR | | | | | | | | | | | | | | | | | | | | | |
| 18 | NP492 | FFFFRRRRRRRR | | | | | | | | | | | | | | | | | | | | | |
| 19 | NP493 | RRRRFFFFRRRR | | | | | | | | | | | | | | | | | | | | | |
| 20 | NP494 | RRRFRFFFRRRR | | | | | | | | | | | | | | | | | | | | | |
| 21 | NP495 | RRRKYRYYYRYRRR | | | | | | | | | | | | | | | | | | | | | |
| 22 | NP496 | RRRFARGAAARAFRR | | | | | | | | | | | | | | | | | | | | | |
| 23 | NP497 | RRRFRRRRRFFF | | | | | | | | | | | | | | | | | | | | | |
| 24 | NP498 | RRRRFFFFRRR | | | | | | | | | | | | | | | | | | | | | |
| | NP432C | RRRFRFFRFRRR-Cysteamine | >250 | >250 | 125 | >250 | 250 | 125 | >250 | >250 | 125 | >250 | 125 | | 250 | 250 | 15.6 | 500 | 250 | 7.8 | 250 | 250 | |
| | NM001 | Cysteamine | >250 | >250 | | >250 | | | >250 | | | | | | | | | | | | | | 62.5 |

Figure 1c

| SEQ. ID No | NP | Sequence | K. pneumoniae NCTC9649 MIC 50 | K. pneumoniae NCTC9649 MIC 90 | K. pneumoniae NCTC9649 MIC | K. pneumoniae NCTC5055 MIC 50 | K. pneumoniae NCTC5055 MIC 90 | K. pneumoniae NCTC5055 MIC | K. pneumoniae NCTC9633 MIC 50 | K. pneumoniae NCTC9633 MIC 90 | K. pneumoniae NCTC9633 MIC | K. pneumoniae PL0263 MIC 50 | K. pneumoniae PL0263 MIC 90 | K. pneumoniae PL0263 MIC | Stn. maltophilia NCTC10257 MIC 50 | Stn. maltophilia NCTC10257 MIC 90 | Stn. maltophilia NCTC10257 MIC | Stn. maltophilia NCTC10498 MIC 50 | Stn. maltophilia NCTC10498 MIC 90 | Stn. maltophilia NCTC10498 MIC | A. xylosoxidans NCTC10807 MIC 50 | A. xylosoxidans NCTC10807 MIC 90 | A. xylosoxidans NCTC10807 MIC | A. xylosoxidans NCTC10808 MIC 50 | A. xylosoxidans NCTC10808 MIC 90 | A. xylosoxidans NCTC10808 MIC |
|---|---|---|---|---|---|---|---|---|---|---|---|---|---|---|---|---|---|---|---|---|---|---|---|---|---|---|
| 1 | NP432 | RRRFRFFFRFRFR | 62.5 | 62.5 | 7.8 | 125 | 125 | 62.5 | 125 | 125 | 15.6 | 62.5 | 62.5 | 15.6 | 15.6 | 15.6 | 7.8 | 15.6 | 15.6 | 7.8 | >250 | >250 | 250 | >250 | >250 | >250 |
| 2 | NP438 | HHFRFFFRFRFR R | | | | | | | | | | | | | | | | | | | | | | | | |
| 3 | NP445 | KKFPWRLRLRY GRR | | | | | | | | | | | | | | | | | | | | | | | | |
| 4 | NP465 | RRRRFRFRFRR R | | | | | | | | | | | | | | | | | | | | | | | | |
| 5 | NP466 | RRRRFRFRFRR R | | | | | | | | | | | | | | | | | | | | | | | | |
| 6 | NP467 | RRRFRFPFRFR R | | | | | | | | | | | | | | | | | | | | | | | | |
| 7 | NP468 | RRRFRFFFRFR R | | | | | | | | | | | | | | | | | | | | | | | | |
| 8 | NP469 | RRRFRFFFRFR A | | | | | | | | | | | | | | | | | | | | | | | | |
| 9 | NP462 | RRRFRFFRRRR | | | | | | | | | | | | | | | | | | | | | | | | |
| 10 | NP470 | RRRRFRFRRR | | | | | | | | | | | | | | | | | | | | | | | | |
| 11 | NP471 | RRRRF-FRRRR | | | | | | | | | | | | | | | | | | | | | | | | |
| 12 | NP472 | RRFRRFRFRRR | | | | | | | | | | | | | | | | | | | | | | | | |
| 13 | NP473 | RRFRFRRRFG | | | | | | | | | | | | | | | | | | | | | | | | |
| 14 | NP474 | RRFGRRFRRFG | | | | | | | | | | | | | | | | | | | | | | | | |
| 15 | NP475 | RRFRRFRRRFG | | | | | | | | | | | | | | | | | | | | | | | | |
| 16 | NP476 | RRFRGFRRRR | | | | | | | | | | | | | | | | | | | | | | | | |
| 17 | NP490 | FRRRRFFFRFR R | | | | | | | | | | | | | | | | | | | | | | | | |
| 18 | NP491 | RRRRRNFFRRR RF | | | | | | | | | | | | | | | | | | | | | | | | |
| 19 | NP492 | FFFFRRRRFFR R | | | | | | | | | | | | | | | | | | | | | | | | |
| 20 | NP493 | RRRFRRFFFRR R | | | | | | | | | | | | | | | | | | | | | | | | |
| 21 | NP494 | FRRRFRFFRR F | | | | | | | | | | | | | | | | | | | | | | | | |
| 22 | NP495 | RRRYRYYYRYR RR | | | | | | | | | | | | | | | | | | | | | | | | |
| 23 | NP496 | RRRAGAAARAR RK | | | | | | | | | | | | | | | | | | | | | | | | |
| 24 | NP487 | RRRFRFFRRFFF F | | | | | | | | | | | | | | | | | | | | | | | | |
|  | NP489 | RRRFFFFRFRRR R | | | | | | | | | | | | | | | | | | | | | | | | |
|  | NP432 | RRRFRFFFRFRR | 250 | 250 | 31.2 5 | 1000 | 1000 | 125 | 250 | 250 | 125 | 250 | 250 | 125 | 256 | 256 | 128 | 512 | 512 | 256 | 512 | 512 | 128 | 512 | 256 | <128 |
|  | MM001 C | Cysteamine | | | | | | | | | | | | | | | | | | | | | | | | |

Figure 2

| SEQ ID. No. | | | MIC (mg/ml) vs Gram + | MIC (mg/ml) vs Gram - |
|---|---|---|---|---|
| 1 | NP432 | RRRFRFFFRFRRR | 7.8 - 62.5 | 15.6 - 62.5 |
| 2 | NP438 | HHHFRFFFRFRRR | >500 | >500 |
| 4 | NP465 | RRRRRFFFRFRRR | 7.8 - 125 | 31.25 - 250 |
| 5 | NP466 | RRRFRFRFRFRRR | 7.8 - 125 | 15.6 - 500 |
| 6 | NP467 | RRRFRFPFRFRRR | 7.8 - 125 | 62.5 - 500 |
| 7 | NP468 | RRFRRFFFRRFRR | 15.6 - 125 | 62.5 - 500 |
| 8 | NP469 | RRRRFFFRRRR | 15.6 - 500 | 250 |
| 9 | NP470 | RRRRFRFRRRR | 125 - 500 | 500 |
| 10 | NP471 | RRRRFPFRRRR | 62.5 - >500 | 500 |
| 11 | NP472 | RRFRRRFRRFR | 31.25 - 500 | 500 |
| 12 | NP473 | RRFRRRFRRFG | 125 - 500 | 500 |
| 13 | NP474 | RRFGRRFRRFG | 125 - 500 | 500 |
| 14 | NP475 | RRFRRFRRRFG | 125 - 500 | 500 |
| 15 | NP476 | RRFRRFRRRFR | 62.5 - 500 | 125 |
| | NP432C | RRRFRFFFRFRRR-cysteamine | 15.6 - 62.5 | 15.6 - 125 |

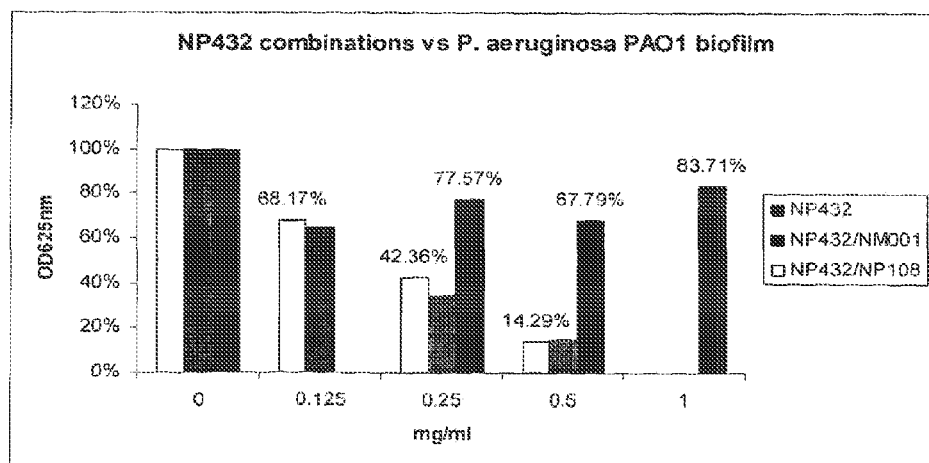

Figure 3: MIC of NP432, NP432 and NM001 and NP432 and NP108 at varying concentrations against P.aeruginosa PA01 biofilm

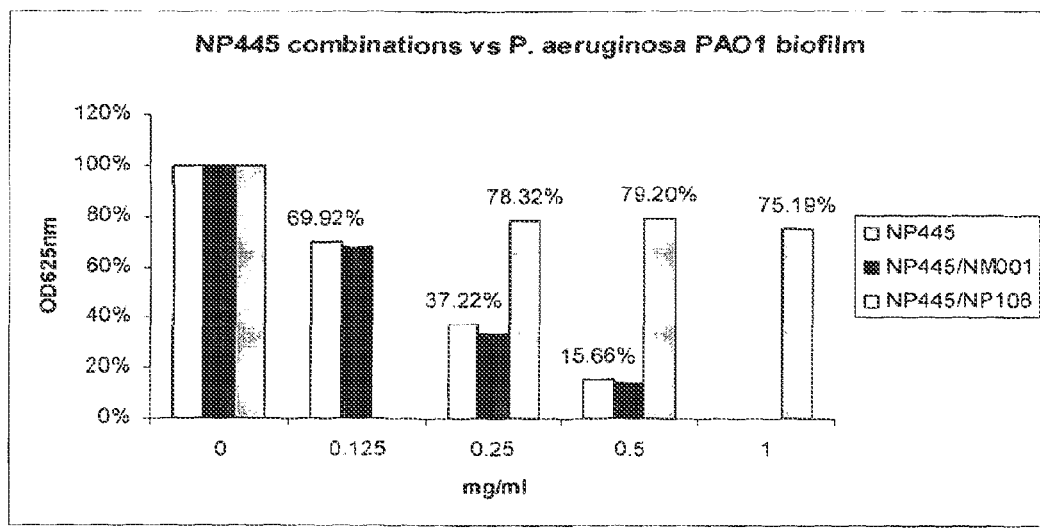
Figure 4: MIC of NP445, NP445 and NM001 and NP445 and NP108 at varying concentrations against P.aeruginosa biofilm Figure 6: MIC of NP445, NP445 and NM001 and NP445 and NP108 at varying concentrations against S. *aureus* biofilm

Figure 7a

```
                        SEQUENCE LISTING

<160> NUMBER OF SEQ ID NOS: 26

<210> SEQ ID NO 1
<211> LENGTH: 13
<212> TYPE: PRT
<213> ORGANISM: Artificial
<220> FEATURE:
<223> OTHER INFORMATION: synthetic peptide

<400> SEQUENCE: 1

Arg Arg Arg Phe Arg Phe Phe Phe Arg Phe Arg Arg Arg
1               5                   10

<210> SEQ ID NO 2
<211> LENGTH: 13
<212> TYPE: PRT
<213> ORGANISM: Artificial
<220> FEATURE:
<223> OTHER INFORMATION: synthetic peptide

<400> SEQUENCE: 2

His His His Phe Arg Phe Phe Phe Arg Phe Arg Arg Arg
1               5                   10

<210> SEQ ID NO 3
<211> LENGTH: 14
<212> TYPE: PRT
<213> ORGANISM: Artificial
<220> FEATURE:
<223> OTHER INFORMATION: sythetic peptide

<400> SEQUENCE: 3

Lys Lys Phe Pro Trp Arg Leu Arg Leu Arg Tyr Gly Arg Arg
1               5                   10

<210> SEQ ID NO 4
<211> LENGTH: 13
<212> TYPE: PRT
<213> ORGANISM: Artificial
<220> FEATURE:
<223> OTHER INFORMATION: synthetic peptide

<400> SEQUENCE: 4

Arg Arg Arg Arg Arg Phe Phe Phe Arg Phe Arg Arg Arg
1               5                   10

<210> SEQ ID NO 5
<211> LENGTH: 13
<212> TYPE: PRT
<213> ORGANISM: Artificial
<220> FEATURE:
<223> OTHER INFORMATION: synthetic peptide
```

```
<400> SEQUENCE: 5

Arg Arg Arg Phe Arg Phe Arg Phe Arg Phe Arg Arg Arg
1               5                   10

<210> SEQ ID NO 6
<211> LENGTH: 13
<212> TYPE: PRT
<213> ORGANISM: Artificial
<220> FEATURE:
<223> OTHER INFORMATION: synthetic peptide

<400> SEQUENCE: 6

Arg Arg Arg Phe Arg Phe Pro Phe Arg Phe Arg Arg Arg
1               5                   10

<210> SEQ ID NO 7
<211> LENGTH: 13
<212> TYPE: PRT
<213> ORGANISM: Artificial
<220> FEATURE:
<223> OTHER INFORMATION: synthetic peptide

<400> SEQUENCE: 7

Arg Arg Phe Arg Arg Phe Phe Phe Arg Arg Phe Arg Arg
1               5                   10

<210> SEQ ID NO 8
<211> LENGTH: 11
<212> TYPE: PRT
<213> ORGANISM: Artificial
<220> FEATURE:
<223> OTHER INFORMATION: synthetic peptide

<400> SEQUENCE: 8

Arg Arg Arg Arg Phe Phe Phe Arg Arg Arg
1               5                   10

<210> SEQ ID NO 9
<211> LENGTH: 11
<212> TYPE: PRT
<213> ORGANISM: Artificial
<220> FEATURE:
<223> OTHER INFORMATION: synthetic peptide

<400> SEQUENCE: 9

Arg Arg Arg Arg Phe Arg Phe Arg Arg Arg
1               5                   10

<210> SEQ ID NO 10
<211> LENGTH: 11
<212> TYPE: PRT
<213> ORGANISM: Artificial
<220> FEATURE:
<223> OTHER INFORMATION: synthetic peptide

<400> SEQUENCE: 10

Arg Arg Arg Arg Phe Pro Phe Arg Arg Arg
1               5                   10

<210> SEQ ID NO 11
<211> LENGTH: 11
<212> TYPE: PRT
<213> ORGANISM: Artificial
<220> FEATURE:
<223> OTHER INFORMATION: synthetic peptide

<400> SEQUENCE: 11
```

Arg Arg Phe Arg Arg Arg Phe Arg Arg Phe Arg
1               5                   10

<210> SEQ ID NO 12
<211> LENGTH: 11
<212> TYPE: PRT
<213> ORGANISM: Artificial
<220> FEATURE:
<223> OTHER INFORMATION: synthetic peptide

<400> SEQUENCE: 12

Arg Arg Phe Arg Arg Arg Phe Arg Arg Phe Gly
1               5                   10

<210> SEQ ID NO 13
<211> LENGTH: 11
<212> TYPE: PRT
<213> ORGANISM: Artificial
<220> FEATURE:
<223> OTHER INFORMATION: synthetic peptide

<400> SEQUENCE: 13

Arg Arg Phe Gly Arg Arg Phe Arg Arg Phe Gly
1               5                   10

<210> SEQ ID NO 14
<211> LENGTH: 11
<212> TYPE: PRT
<213> ORGANISM: Artificial
<220> FEATURE:
<223> OTHER INFORMATION: synthetic peptide

<400> SEQUENCE: 14

Arg Arg Phe Arg Arg Phe Arg Arg Arg Phe Gly
1               5                   10

<210> SEQ ID NO 15
<211> LENGTH: 11
<212> TYPE: PRT
<213> ORGANISM: Artificial
<220> FEATURE:
<223> OTHER INFORMATION: synthetic peptide

<400> SEQUENCE: 15

Arg Arg Phe Arg Arg Phe Arg Arg Arg Phe Arg
1               5                   10

<210> SEQ ID NO 16
<211> LENGTH: 13
<212> TYPE: PRT
<213> ORGANISM: Artificial
<220> FEATURE:
<223> OTHER INFORMATION: synthetic peptide

<400> SEQUENCE: 16

Phe Arg Arg Arg Arg Phe Phe Phe Arg Phe Arg Arg Arg
1               5                   10

<210> SEQ ID NO 17
<211> LENGTH: 13
<212> TYPE: PRT
<213> ORGANISM: Artificial
<220> FEATURE:
<223> OTHER INFORMATION: syntheic peptide

<400> SEQUENCE: 17

Arg Arg Arg Arg Arg Phe Phe Phe Arg Arg Arg Arg Phe
1               5                   10

<210> SEQ ID NO 18
<211> LENGTH: 13
<212> TYPE: PRT
<213> ORGANISM: Artificial
<220> FEATURE:
<223> OTHER INFORMATION: synthetic peptide

<400> SEQUENCE: 18

Phe Phe Phe Phe Arg Arg Arg Arg Arg Phe Arg Arg Arg
1               5                   10

<210> SEQ ID NO 19
<211> LENGTH: 13
<212> TYPE: PRT
<213> ORGANISM: Artificial
<220> FEATURE:
<223> OTHER INFORMATION: synthetic peptide

<400> SEQUENCE: 19

Arg Arg Arg Arg Phe Phe Phe Phe Phe Arg Arg Arg Arg
1               5                   10

<210> SEQ ID NO 20
<211> LENGTH: 13
<212> TYPE: PRT
<213> ORGANISM: Artificial
<220> FEATURE:
<223> OTHER INFORMATION: synthetic peptide

<400> SEQUENCE: 20

Phe Arg Arg Arg Arg Phe Phe Phe Arg Arg Arg Arg Phe
1               5                   10

<210> SEQ ID NO 21
<211> LENGTH: 13
<212> TYPE: PRT
<213> ORGANISM: Artificial
<220> FEATURE:
<223> OTHER INFORMATION: synthetic peptide

<400> SEQUENCE: 21

Arg Arg Arg Tyr Arg Tyr Tyr Tyr Arg Tyr Arg Arg Arg
1               5                   10

<210> SEQ ID NO 22
<211> LENGTH: 13
<212> TYPE: PRT
<213> ORGANISM: Artificial
<220> FEATURE:
<223> OTHER INFORMATION: synthetic peptide

<400> SEQUENCE: 22

Arg Arg Arg Ala Arg Ala Ala Ala Arg Ala Arg Arg Arg
1               5                   10

<210> SEQ ID NO 23
<211> LENGTH: 13
<212> TYPE: PRT
<213> ORGANISM: Artificial
<220> FEATURE:
<223> OTHER INFORMATION: synthetic peptide

<400> SEQUENCE: 23

Arg Arg Arg Phe Arg Arg Arg Arg Arg Phe Phe Phe Phe

```
<210> SEQ ID NO 24
<211> LENGTH: 13
<212> TYPE: PRT
<213> ORGANISM: Artificial
<220> FEATURE:
<223> OTHER INFORMATION: synthetic peptide

<400> SEQUENCE: 24

Arg Arg Arg Phe Phe Phe Phe Phe Phe Phe Arg Arg Arg
1               5                   10

<210> SEQ ID NO 25
<211> LENGTH: 13
<212> TYPE: PRT
<213> ORGANISM: Artificial
<220> FEATURE:
<223> OTHER INFORMATION: synthetic peptide

<400> SEQUENCE: 25

Arg Arg Arg Phe Arg Phe Phe Phe Arg Phe Arg Arg Arg
1               5                   10

<210> SEQ ID NO 26
<211> LENGTH: 14
<212> TYPE: PRT
<213> ORGANISM: Artificial
<220> FEATURE:
<223> OTHER INFORMATION: synthetic peptide

<400> SEQUENCE: 26

Lys Lys Pro Arg Arg Lys Pro Arg Arg Pro Lys Arg Lys Lys
1               5                   10
```

COMPOUNDS AND THEIR USE

CROSS-REFERENCE TO RELATED APPLICATIONS

This application is a U.S. National Phase of International Patent Application No. PCT/GB2011/000480 filed Mar. 30, 2011 which claims priority to International Patent Application No. PCT/GB2010/000631 filed 31 Mar. 2010 and also claims priority to United Kingdom application no. 1016733.6 filed 5 Oct. 2010 and also claims priority to provisional application No. 61/390,080 filed 5 Oct. 2010, the disclosures of which are incorporated herein by reference in their entirety for all purposes.

FIELD OF THE INVENTION

The present invention relates to peptides and their use in the treatment of microbial infections, in particular bacterial infections. There is also provided a method of medical treatment.

BACKGROUND TO THE INVENTION

Antimicrobial peptides are key effector molecules of the innate immune system and integral components of the first line of defence against microbial infections of all eukaryotic organisms. A number of prokaryotic organisms also utilise antimicrobial peptides as means to compete against challenge from other microorganisms. Many antimicrobial peptides are characterised by cationic properties that facilitate interactions with the negatively charged phospholipids of the microbial membrane which then lead to microbial lysis and death following membrane permeabilisation. For example, it has been shown that antimicrobial peptide molecules can aggregate and form voltage dependent channels in the lipid bilayer resulting in the permeabilisation of both the inner and outer membrane of the microorganism (Lehrer, R. I., J. Clin. Investigation, 84:553 (1989)). The amphiphilic nature of these molecules may also facilitate the insertion of the hydrophobic residue into the lipid bilayer by electrostatic attraction while the polar residues project into and above the membrane.

Drug resistant microorganisms, especially bacteria, are becoming increasingly problematic as infection rates continue to rise and effective methods of control become more and more limited. Prolific use of antibiotics over the last 50 or so years, together with the indiscriminate prescribing of antibiotics and patient non-compliance with treatment regimes, has selected for microorganisms that have developed or acquired means of overcoming the effects of antibiotics. The transmission and control of drug-resistant organisms is becoming one of the most significant problems within healthcare.

All Gram positive genera, including *Staphylococcus* spp., *Enterococcus* spp., *Listeria* spp., *Clostridium* spp., *Corynebacterium* spp., *Nocardia* spp., *Bacillus* spp. and *Streptococcus* spp., including those that have developed or obtained varying levels of resistance to antibiotics such as methicillin (meticillin), are of particular interest as are the Gram negative genera *Escherichia* spp., *Pseudomonas* spp., *Klebsiella* spp. and *Acetinobacter* spp. Other Gram negative pathogens of interest include the Enterobacteriaceae (especially those producing either extended-spectrum β-lactamase (ESBL) or carbapenemase). Coagulase-negative *Staphylococci*, such as *S. epidermidis*, have also emerged as important drug-resistant nosocomial pathogens. The treatment options for infections contributed to or caused by methicillin or multi-drug resistant bacteria are now limited and there is an urgent need to discover new therapies which inhibit or kill such organisms. Other bacterial pathogens of particular interest include *Mycobacterium* spp., e.g. *Mycobacterium tuberculosis*; *Enterobacter* spp.; *Campylobacter* spp.; *Salmonella* spp.; *Helicobacter* spp., e.g. *Helicobacter pylori*; *Neisseria* spp., e.g. *Neisseria gonorrhea*, *Neisseria meningitidis*; *Borrelia burgdorferi*; *Shigella* spp., e.g. *Shigella flexnerii*; *Haemophilus* spp., e.g. *Haemophilus influenzae*; *Chlamydia* spp., e.g. *Chlamydia trachomatis*, *Chlamydia pneumoniae*, *Chlamydia psittaci*; *Francisella tularensis*; *Yersinia* spp., e.g. *Yersinia pestis*; *Treponema* spp.; *Burkholderia* spp.; e.g. *Burkholderia mallei* and *B. pseudomallei*.

*Pseudomonas aeruginosa* is an opportunistic pathogen that causes, respiratory tract infections, urinary tract infections, dermatitis, soft tissue infections, bacteraemia and a variety of systemic infections, particularly in patients with severe burns and in cancer and AIDS patients who are immunosuppressed. Respiratory infections caused by *Pseudomonas aeruginosa* occur almost exclusively in individuals with a compromised lower respiratory tract or a compromised systemic defence mechanism (for example in patients with cystic fibrosis or chronic obstructive pulmonary disease). Primary pneumonia occurs in patients with chronic lung disease and congestive heart failure. Bacteraemic pneumonia commonly occurs in neutropenic cancer patients undergoing chemotherapy. Lower respiratory tract colonisation of cystic fibrosis patients by mucoid strains of *Pseudomonas aeruginosa* is common and difficult to treat. There is a need to develop an effective means of treating *Pseudomonas aeruginosa* infections.

*Staphylococcus aureus* is an opportunistic pathogen that is normally encountered on the skin and in the nose of many healthy people where it lives completely harmlessly. *S. aureus* can, however, cause problems when it is able to enter the body causing abscesses, boils, pimples, impetigo and wound infections, whether accidental or surgical. If the infection gets into the bloodstream and travel to different parts of the body it can cause blood poisoning (septicaemia), bone infection (osteomyelitis), heart valve infection (endocarditis) and lung infection (pneumonia). MRSA is a type of *S. aureus* that is resistant to many commonly prescribed antibiotics, including methicillin (~40% of *S. aureus* infections in the UK are resistant to methicillin and other antibiotics), and is commonly referred to in the popular press as a "superbug". MRSA is one of the most prevalent microbes involved with healthcare-associated infections. Infections are normally confined to hospitals, and in particular to vulnerable and/or debilitated patients, including patients in intensive care units, burns units and orthopaedic wards. MRSA is more difficult to treat because many antibiotics are ineffective, and those that are effective often need to be given at much higher doses, intravenously, over prolonged periods of time (several weeks) thereby highlighting the need to develop alternative antimicrobial therapies.

Since microbial pathogens do not readily acquire resistance to cationic peptides, despite evolutionary pressure from millions of years of co-existence, they remain attractive therapeutic targets. In our co-pending applications, WO 2006/018652 and WO 2008/093058, we describe the identification of peptides that can be used to treat microbial infections, including bacterial infections.

A microbial biofilm is a community of microbial cells embedded in an extracellular matrix of polymeric substances and adherent to a biological or a non-biotic surface. A range of microorganisms (bacteria, fungi, and/or protozoa, with associated bacteriophages and other viruses) can be found in these biofilms. Biofilms are ubiquitous in nature and are commonly found in a wide range of environments. Biofilms are being increasingly recognised by the scientific and medical community as being implicated in many infections, and especially their contribution to the recalcitrance of infection treatment.

Biofilm formation is not limited solely to the ability of microbes to attach to a surface. Microbes growing in a biofilm are able to interact more between each other than with the actual physical substratum on which the biofilm initially developed. For example, this phenomenon favours conjugative gene transfer, which occurs at a greater rate between cells in biofilms than between planktonic cells. This represents an increased opportunity for horizontal gene transfer between bacteria, and is important because this can facilitate the transfer of antibiotic resistance or virulence determinant genes from resistant to susceptible microbes. Bacteria can communicate with one another by a system known as quorum sensing, through which signalling molecules are released into the environment and their concentration can be detected by the surrounding microbes. Quorum sensing enables bacteria to co-ordinate their behaviour, thus enhancing their ability to survive. Responses to quorum sensing include adaptation to availability of nutrients, defence against other microorganisms which may compete for the same nutrients and the avoidance of toxic compounds potentially dangerous for the bacteria. It is very important for pathogenic bacteria during infection of a host (e.g. humans, other animals or plants) to co-ordinate their virulence in order to escape the immune response of the host in order to be able to establish a successful infection.

Biofilm formation plays a key role in many infectious diseases, such as cystic fibrosis and periodontitis, in bloodstream and urinary tract infections and as a consequence of the presence of indwelling medical devices. The suggested mechanisms by which biofilm-associated microorganisms elicit diseases in their host include the following: (i) delayed penetration of the antimicrobial agent through the biofilm matrix, (ii) detachment of cells or cell aggregates from indwelling medical device biofilms, (iii) production of endotoxins, (iv) resistance to the host immune system, (v) provision of a niche for the generation of resistant organisms through horizontal gene transfer of antimicrobial resistance &/or virulence determinant genes, and (vi) altered growth rate (i.e. metabolic dormancy) (Donlan and Costerton, Clin Microbiol Rev 15: 167-193, 2002; Parsek and Singh, Annu Rev Microbiol 57: 677-701, 2003; Costerton J W, Resistance of biofilms to stress. In 'The biofilm primer'. (Springer Berlin Heidelberg). pp. 56-64.2007).

Recent experimental evidence has indicated the existence within biofilms of a small sub-population of specialized non-metabolising persister cells (dormant cells). It is thought that these cells may be responsible for the high resistance/tolerance of biofilm to antimicrobial agents. Multi-drug-tolerant persister cells are present in both planktonic and biofilm populations and it appears that yeasts and bacteria have evolved analogous strategies that assign the function of survival to this sub-population. The protection offered by the polymeric matrix allows persister cells to evade elimination and serve as a source for re-population. There is evidence that persisters may be largely responsible for the multi-drug tolerance of microbial biofilms (LaFleur et al., Antimicrob Agents Chemother. 50: 3839-46, 2006; Lewis, Nature Reviews Microbiology 5, 48-56 2007).

There is a requirement, therefore, for further agents that can be used to treat microbial infections. In particular, there remains a pressing need for further antimicrobial actives that can be used in the treatment of bacterial infections such as those caused by *Staphylococci, Streptococci, Acinetobacter* spp., *Klebsiella* spp., *E. coli* and *Pseudomonas* spp. There is also an urgent requirement for better therapies for preventing biofilm formation and treating conditions associated with microbial biofilms.

The present inventors have identified peptides that, surprisingly, have improved antimicrobial activity over natural antimicrobial peptides, such as the defensins, cathelicidins, etc. The claimed compounds have potent antimicrobial properties, whilst exhibiting low toxicity in vitro and in vivo to animals and humans.

STATEMENTS OF THE INVENTION

According to a first aspect of the present invention there is provided a peptide wherein at least 75% of the amino acids of the peptide are arginine and phenylalanine amino acids, at least 50% of the amino acids being arginine amino acids and at least 15% of the amino acids being phenylalanine amino acids.

The peptides of the invention are useful, inter alia, in the treatment or prevention of microbial infections, in particular bacterial infections such as, but not limited to, those caused by *Staphylococcus* spp. and *Pseudomonas* spp. The peptides of the present invention are also useful in the prevention and treatment of biofilm infections caused by these and other bacteria.

Generally at least 80% of the amino acids in the peptide are arginine and phenylalanine amino acids, suitably at least 90%, more suitably at least 95%, typically around 99% of the amino acids in the peptide are arginine and phenylalanine amino acids. According to one embodiment, all of the amino acids in the peptide are arginine and phenylalanine.

Generally at least 55% of the amino acids in the peptide are arginine amino acids, suitably at least 60% (for example 61%), more suitably at least 65%, typically around 70% of the amino acids in the peptide are arginine amino acids.

Generally at least 20% of the amino acids in the peptide are phenylalanine amino acids, suitably at least 25%, more suitably at least 30%, typically around 30 to 40% (for example 38%) of the amino acids in the peptide are phenylalanine amino acids.

The amino acids of the peptide of the present invention may be D or L-amino acids. The amino acids may be optical isomers of a cationic amino acid as defined herein for example D or L-amino acids. The amino acids may be naturally occurring or synthetic. The invention also includes known isomers (structural, stereo-, conformational & configurational) and structural analogues of the above amino acids, and those modified either naturally (e.g. post-translational modification) or chemically, including, but not exclusively, phosphorylation, glycosylation, sulfonylation and/or hydroxylation.

According to one embodiment of the present invention, the peptide consists of arginine and phenylalanine amino acids optionally with up to five non-arginine and non-phenylalanine substitutions. Generally the peptide consists of arginine and phenylalanine amino acids with zero, one, two or three non-arginine and non-phenylalanine substitutions, typically zero, one or two substitutions; advantageously zero or one substitution.

According to one embodiment, the peptide consists of arginine and phenylalanine amino acids.

Typically the peptide of the present invention may comprise 1 to 5 substitutions, suitably 1 to 3 substitutions, generally one substitution. The substitution(s) may be terminal or non-terminal.

The substitutions may consist of amino acids or non-amino acids. The substitutions may be charged or uncharged. Typically, one or more of the substitutions are uncharged amino acids. Alternatively or additionally one or more of the substitutions may be charged amino acids, in particular cationic amino acids. One or more of the amino acid substitutions may be hydrophobic.

Where one or more of the substitution are amino acid substitutions, they may be charged or uncharged amino acids. The amino acid substitutions may be naturally occurring, or non-naturally occurring, synthesised amino acid substitutions.

Generally the substitutions consist of one or more hydrophobic amino acid, and/or one or more cationic amino acid.

As used herein, the term "hydrophobic" refers to an amino acid having a side chain that is uncharged at physiological pH, that is not polar and that is generally repelled by aqueous solution.

Generally a hydrophobic amino residue has a hydrophobicity greater than or equal to −1.10 and a charge less than or equal to 0.

As used herein, the term "cationic" refers to amino acids having a net charge that is greater than or equal to 0. Generally the term "cationic" refers to amino acids having a net charge that is greater than zero.

Typical hydrophobic amino acid substitutions include glycine, leucine, proline, alanine, tryptophan, valine, isoleucine, methionine, tyrosine and threonine.

Typical cationic amino acid substitutions include ornithine, histidine and lysine.

According to one embodiment, the peptide comprises one or more cysteine amino acids, in particular one or two terminal cysteine residues.

According to one embodiment, the peptide comprises one or more substitution selected from the group lysine, proline, glycine and histidine.

Advantageously, the peptide consists of arginine, phenylalanine and one of the group consisting of lysine, proline, glycine and histidine. Advantageously the group consists of proline and glycine.

Generally the peptide does not comprise the amino acids aspartic acid, glutamic acid, asparagines, glutamine or serine, but certain peptides of the invention may have activity even though these amino acids are present.

In addition, the amino acid sequence of a peptide can be modified so as to result in a peptide variant that includes the substitution of at least one amino acid residue in the peptide for another amino acid residue, including substitutions that utilise the D rather than L form.

One or more of the residues of the peptide can be exchanged for another to alter, enhance or preserve the biological activity of the peptide. Such a variant can have, for example, at least approximately 10% of the biological activity of the corresponding non-variant peptide. Conservative amino acids are often utilised, i.e. substitutions of amino acids with similar chemical and physical properties as described above.

Hence, for example, conservative amino acid substitutions may involve exchanging one cationic amino acid for another, for example exchanging arginine for lysine, ornithine or histidine. Alternatively or additionally, phenylalanine may be exchanged for glycine, leucine, proline, alanine, tryptophan, valine, isoleucine, methionine, tyrosine or threonine. After the substitutions are introduced, the variants are screened for biological activity.

The peptide of the present invention may comprise from 2 to 200 amino acids, for example 3, 4, 5, 6, or 7 up to 100 amino acids, including 3, 4, 5, 6, or 7 up to 10, 15, 20, 25, 30, 35, 40, 45 or 50 amino acids. According to one embodiment, the antimicrobial peptide comprises 3 or 4 to 50 amino acids.

The peptide may comprise 100 to 200 amino acids, 20 to 100, 20 and 45 amino acids such as 20, 25, 30, 35, 40, 42 or 45 amino acids. The peptide may comprise between 3 and 15 amino acids, for example 5 to 15 amino acids for example 13 to 15 amino acids.

Typically, the peptide comprises 5 to 20 amino acids; suitably 5 to 15, more suitably 7 to 15, generally 10 to 15 amino acids, including 11 to 13 amino acids.

According to one embodiment, the peptide consists of 10 to 15 amino acids, in particular 11 to 13 amino acids.

The peptide may typically comprise 5 to 50 arginine amino acids, suitably 5 to 30, more suitably 5 to 20, generally 7 to 10 arginine amino acids.

The peptide may comprise 1 to 20 phenylalanine amino acids, typically 1 to 15, suitably 2 to 10, more suitably 2 to 5 phenylalanine amino acids.

Generally the peptide comprises an arginine backbone with phenylalanine substitutions therein.

Generally the peptide comprises at least one portion of 3 to 20 contiguous arginine amino acids, typically at least one portion of 3 to 10 contiguous arginine amino acids, suitably at least one portion of 3 to 5 contiguous arginine amino acids. Alternatively or additionally the peptide may comprise at least one portion of 5 to 10 contiguous arginine amino acids.

Generally the peptide comprises at least one portion of 1 to 5 contiguous phenylalanine amino acids, typically at least one portion of 3 to 5 contiguous phenylalanine amino acids, suitably the peptide comprises at least one portion of 3 contiguous phenylalanine amino acids.

According to one embodiment, the peptide comprises more than one phenylalanine portion; where each phenylalanine portion comprises one or more phenylalanine amino acid. Generally the peptide comprises two or three phenylalanine portions.

According to one embodiment the peptide does not comprise terminal phenylalanine amino acids.

According to one embodiment the peptide comprises one terminal phenylalanine amino acid only for example an N-terminal phenylalanine Preferably the peptide does not comprise terminal phenylalanine amino acids at both ends of the peptide.

Typically the peptide comprises arginine amino acid portions at one or both ends, suitably arginine amino acid portions having 1 to 5 arginine amino acids. Alternatively, the peptide may comprise one or two terminal non-arginine and non-phenylalanine substitutions. Suitable terminal substitutions include the substitutions described above, in particular histidine, cysteamine and lysine.

The peptide may comprise a phenylalanine amino acid at the C- or N-terminus and an arginine amino acid at the respective N- or C-terminus.

According to one embodiment the peptide comprises a C-terminal arginine amino acids and an N-terminal phenylalanine amino acid.

According to one embodiment the peptide does not comprise a sequence (for example 2 or more) phenylalanine amino acids at the N terminus The peptide of the present invention may be symmetrical or non-symmetrical.

Preferably the peptide is acyclic. The peptide may be straight chained i.e. linear or branched. The term "peptide" as used herein means, in general terms, a plurality of amino acid residues joined together by peptide bonds. It is used interchangeably and means the same as polypeptide and protein.

According to one embodiment of the present invention, the peptide comprises an amino acid sequence selected from the group RRRFRFFFRFRRR (SEQ ID NO: 1), HHHFRFFFR-FRRR (SEQ ID NO: 2), KKFPWRLRLRYGRR (SEQ ID NO: 3), RRRRRFFFRFRRR (SEQ ID NO: 4), RRRFRFR-FRFRRR (SEQ ID NO: 5), RRRFRFPFRFRRR (SEQ ID NO: 6), RRFRRFFFRRFRR (SEQ ID NO: 7), RRRRFFFR-RRR (SEQ ID NO: 8), RRRRFRFRRRR (SEQ ID NO: 9), RRRRFPFRRRR (SEQ ID NO: 10), RFRRRFRRFR (SEQ ID NO: 11), RRFRRRFRRFG (SEQ ID NO: 12), RRFGR-RFRRFG (SEQ ID NO: 13), RRFRRFRRRFG (SEQ ID NO: 14), RRFRRFRRRFR (SEQ ID NO: 15), FRRRRFFFR-FRRR (SEQ ID NO: 16), RRRRRFFFRRRRF (SEQ ID NO: 17), FFFFRRRRRFRRR (SEQ ID NO: 18), RRRRFFFFFR-RRR (SEQ ID NO: 19), FRRRRFFFRRRRF (SEQ ID NO: 20), RRRYRYYYRYRRR (SEQ ID NO: 21), RRRARAAARARRR (SEQ ID NO: 22), RRRFR-RRRRFFFF (SEQ ID NO: 23), RRRFFFFFFFRRR (SEQ ID NO: 24) and RRRFRFFFRFRRR (SEQ ID NO: 25)-cysteamine. The peptides may consist essentially of these amino acid sequences.

According to one embodiment of the present invention, the peptide comprises an amino acid sequence selected from the group RRRFRFFFRFRRR (SEQ ID NO: 1) (NP432), FRRRRFFFRFRRR (SEQ ID NO: 16) (NP490), RRRRFFFFFRRRR (SEQ ID NO: 19) (NP493) and RRRFR-RRRRFFFF (SEQ ID NO: 23) (NP497).

According to a second aspect of the present invention, the peptide comprises a mixture of hydrophobic and cationic amino acids. In particular, the hydrophobic amino acids are selected from the group consisting of glycine, leucine, phenylalanine, proline, alanine, tryptophan, valine, isoleucine, methionine, tyrosine and threonine.

The peptide of this embodiment generally comprises arginine amino acids but does not necessarily comprise phenylalanine amino acids.

Typically the hydrophobic amino acids are selected from the group consisting of phenylalanine, tryptophan, tyrosine and glycine.

In particular, the cationic amino acids are selected from the group consisting of ornithine, histidine, arginine and lysine. Typically the cationic amino acids are selected from the group consisting of arginine and lysine.

According to one embodiment, the peptide comprises lysine, phenylalanine and arginine amino acids.

According to a further embodiment, the peptide comprises lysine, arginine, phenylalanine, proline, tryptophan, tyrosine and glycine amino acids. Although the peptides of the present invention do not generally include glutamine amino acids, some such peptides may exhibit activity. This peptide may include one or two glutamine amino acids.

According to one embodiment, the peptides described above may consist of the specified amino acids with zero, one or two substitutions. Generally the peptides of the present invention consist of the specified amino acids. Alternatively, the peptides of this embodiment of the present invention may comprise substitutions as detailed above.

The peptides of the second embodiment may comprise an amino acid sequence selected from the group consisting of KKPRRKPRRPKRKK (SEQ ID NO: 26) (NP449) and KKF-PWRLRLRYGRR (SEQ ID NO: 3) (NP445).

The peptides of the invention are generally synthetic peptides. The peptides may be isolated, purified peptides or variants thereof, which can be synthesised in vitro, for example, by a solid phase peptide synthetic method, by enzyme catalysed peptide synthesis or with the aid of recombinant DNA technology.

To identify active peptides that have little or no undesired toxicity for mammalian cells, individual peptides, or libraries of peptides, can be made and the individual peptides or peptides from those libraries can be screened for antimicrobial activity and toxicity, including, but not limited to, antifungal, antibacterial, antiviral, antiprotozoal, anti-parasitic activity and toxicity.

The peptides of the invention can exist in different forms, such as free acids, free bases, esters and other prodrugs, salts and tautomers, for example, and the invention includes all variant forms of the compounds.

Thus, the invention encompasses the salt or pro-drug of a peptide or peptide variant of the invention.

Composition

According to a further aspect of the present invention, there is provided a composition comprising one or more of the peptides as described above, together with one or more adjuvants or excipients.

According to one embodiment, the composition may comprise two or more peptides of the present invention. Advantageously, the composition comprises one, two or three peptides of the present invention.

The agents of the invention may be administered in the form of pharmaceutically acceptable salts. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., US, 1985, p. 1418, the disclosure of which is hereby incorporated by reference; see also Stahl et al, Eds, "*Handbook of Pharmaceutical Salts Properties Selection and Use*", Verlag Helvetica Chimica Acta and Wiley-VCH, 2002. The phrase "pharmaceutically acceptable" is employed herein to refer to those compounds, materials, compositions, and/or dosage forms which are, within the scope of sound medical judgment, suitable for use in contact with the tissues of human beings or, as the case may be, an animal without excessive toxicity, irritation, allergic response, or other problem or complication, commensurate with a reasonable benefit/risk ratio.

The invention thus includes pharmaceutically-acceptable salts of the disclosed compounds wherein the parent compound is modified by making acid or base salts thereof for example the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Salts of carboxyl groups of a peptide or peptide variant of the invention may be prepared in the usual manner by contacting the peptide with one or more equivalents of a desired base such as, for example, a metallic hydroxide base, e.g. sodium hydroxide; a metal carbonate or bicarbonate such as, for example, sodium carbonate or bicarbonate; or an amine base such as, for example, triethylamine, triethanolamine and the like.

N-acyl derivatives of an amino group of the peptide or peptide variants of the invention may be prepared by utilising an N-acyl protected amino acid for the final condensation, or by acylating a protected or unprotected amino acid. O-acyl derivatives may be prepared, for example, by acylation of a free hydroxy peptide or peptide resin. Either acylation may be carried out using standard acylating reagents such as acyl halides, anhydrides, acyl imidazoles, and the like.

The invention includes prodrugs for the active pharmaceutical species of the described peptides, for example in which one or more functional groups are protected or derivatised but can be converted in vivo to the functional group, as in the case of esters of carboxylic acids convertible in vivo to the free acid, or in the case of protected amines, to the free amino group. The term "prodrug," as used herein, represents particular structures which are rapidly transformed in vivo to the parent structure, for example, by hydrolysis in blood. A thorough discussion is provided in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987; H Bundgaard, ed, Design of Prodrugs, Elsevier, 1985; and Judkins, et al. Synthetic Communications, 26(23), 4351-4367 (1996), each of which is incorporated herein by reference.

Prodrugs therefore include drugs having a functional group which has been transformed into a reversible derivative thereof. Typically, such prodrugs are transformed to the active drug by hydrolysis. Prodrugs also include compounds convertible to the active drug by an oxidative or reductive reaction. As examples may be mentioned the following: oxidative activation, —N- and O-dealkylation, oxidative deamination, N-oxidation, epoxidation, reductive activation, azo reduction, sulfoxide reduction, disulfide reduction, Bioreductive alkylation and—Nitro reduction.

Also to be mentioned as metabolic activations of prodrugs are nucleotide activation, phosphorylation activation and decarboxylation activation.

The use of protecting groups is fully described in "Protective Groups in Organic Chemistry", edited by J W F McOmie, Plenum Press (1973), and "Protective Groups in Organic Synthesis", 2nd edition, T W Greene & P G M Wutz, Wiley-Interscience (1991).

Thus, it will be appreciated by those skilled in the art that, although protected derivatives of the described peptides may not possess pharmacological activity as such, they may be administered, for example parenterally or orally, and thereafter metabolised in the body to form compounds which are pharmacologically active. Such derivatives are therefore examples of "prodrugs". AU prodrugs of the described compounds are included within the scope of the invention.

The composition of the present invention also includes one or more pharmaceutically acceptable carriers, excipients, adjuvants or diluents. The phrase "pharmaceutically acceptable" is employed herein to refer to those compounds, materials, compositions, and/or dosage forms which are, within the scope of sound medical judgment, suitable for use in contact with the tissues of human beings or, as the case may be, an animal without excessive toxicity, irritation, allergic response, or other problem or complication, commensurate with a reasonable benefit/risk ratio.

When the therapeutic peptides of the invention are prepared for oral administration, they are generally combined with a pharmaceutically acceptable carrier, diluent or excipient to form a pharmaceutical formulation, or unit dosage form. For oral administration, the peptides may be present as a powder, a granular formation, a solution, a suspension, an emulsion or in a natural or synthetic polymer or resin for ingestion of the active ingredients from a chewing gum. The active peptides may also be presented as a bolus, electuary or paste. Orally administered therapeutic peptides of the invention can also be formulated for sustained release, e.g., the peptides can be coated, micro-encapsulated, or otherwise placed within a sustained delivery device. The total active ingredients in such formulations comprise from 0.1 to 99.9% by weight of the formulation.

Thus, one or more suitable unit dosage forms comprising the therapeutic peptides of the invention can be administered by a variety of routes including oral, parenteral (including subcutaneous, intravenous, intramuscular and intraperitoneal), rectal, dermal, transdermal, intrathoracic, intrapulmonary, mucosal, intraocular and intranasal (respiratory) routes. The therapeutic peptides may also be formulated in a lipid formulation or for sustained release (for example, using microencapsulation, see WO 94/07529, and U.S. Pat. No. 4,962,091 incorporated herein by reference). The formulations may, where appropriate, be conveniently presented in discrete unit dosage forms and may be prepared by any of the methods well-known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

Pharmaceutical formulations containing the therapeutic peptides of the invention can be prepared by procedures known in the art using well-known and readily available ingredients. For example, the peptide can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatine, and polyvinylpyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the peptides of the invention can include buffering agents such as calcium carbonate, magnesium oxide and magnesium carbonate. Suitable buffering agents may also include acetic acid in a salt, citric acid in a salt, boric acid in a salt and phosphoric acid in a salt. Caplets and tablets can also include inactive ingredients such as cellulose, pregelatinized starch, silicon dioxide, hydroxyl propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatine capsules containing at least one peptide of the invention can contain inactive ingredients such as gelatine, microcrystalline cellulose, sodium lauryl sulphate, starch, talc, and titanium dioxide, and the like, as well as liquid vehicles such as polyethylene glycols (PEGs) and vegetable oil. Moreover, enteric-coated caplets or tablets containing one or more peptides of the invention are designed to resist disintegration in the stomach and dissolve in the more neutral to alkaline environment of the duodenum.

The therapeutic peptides of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic peptides of the invention can also take the form of an aqueous or anhydrous solution or dispersion, or alternatively the form of an emulsion or suspension or salve.

Thus, the therapeutic peptides may be formulated for parenteral administration (e.g. by injection, for example, bolus injection or continuous infusion) and may be presented in unit dose form in ampules, pre-filled syringes, small volume infusion containers or in multi-dose containers. As noted above, preservatives can be added to help maintain the shelve life of the dosage form. The active peptides and other ingredients may form suspensions, solutions, or emulsions in oily or aqueous vehicles, and may contain formulatory agents such as suspending, stabilizing and/or dispersing agents. Alternatively, the active peptides and other ingredients may be in powder form, obtained by aseptic isolation of sterile solid or by lyophilization from solution for constitution with a suitable vehicle, e.g., sterile, pyrogen-free water before use.

It is possible to add, if necessary, an adjuvant chosen from antioxidants, surfactants, other preservatives, film-forming, keratolytic or comedolytic agents, perfumes, flavorings and colourings. Antioxidants such as t-butylhydroquinone, butylated hydroxyanisole, butylated hydroxytoluene and [alpha]-tocopherol and its derivates can be added.

These formulations can contain pharmaceutically acceptable carriers, vehicles and adjuvants that are well-known in the art. It is possible, for example, to prepare solutions using one or more organic solvent(s) that is/are acceptable from the physiological standpoint, chosen, in addition to water, from solvents such as acetone, acetic acid, ethanol, isopropyl alcohol, dimethyl sulphoxide, glycol ethers such as the products sold under the name "Dowanol", polyglycols and polyethylene glycols, C1-C4 alkyl esters of short-chain acids, ethyl or isopropyl lactate, fatty acid triglycerides such as the products marketed under the name "Miglyol", isopropyl mytrisate, animal, mineral and vegetable oils and polysiloxanes.

Preferably, the composition is in the form of a pharmaceutical formulation of the therapeutic peptides of the invention can also take the form of a solvent or diluent comprising the peptide. Solvents or diluents may include acid solutions, dimethylsulphone, N-(2-mercaptopropionyl) glycine, 2-n-nonyl-1,3-dioxolane and ethyl alcohol. Preferably the solvent/diluent is an acidic solvent, for example, acetic acid, citric acid, boric acid, lactic acid, propionic acid, phosphoric acid, benzoic acid, butyric acid, malic acid, malonic acid, oxalic acid, succinic acid or tartaric acid.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

More preferably, the solvent is an acetic acid solution. The solvent, for example acetic acid solution, may be present in the composition at a concentration of less than 1%, 0.5%, 0.25%, 0.1%, 0.05% or 0.01% acid, for example acetic acid.

The composition of the present invention may comprise one or more additional antimicrobial agents. In particular, the composition of the present invention may comprise one or more additional antibacterial agents.

Also contemplated are combination products that include one or more peptides of the present invention and one or more other antimicrobial, in particular one or more other antibacterial agent. The composition of the present invention may comprise one or more of cysteamine (NM001), polyarginine and polylysine, such as 10 to 20 kDa poly-L-lysine hydrobromide (NP108), 15 to 30 kDa poly-L-lysine hydrochloride (NP101) and 5 to 15 kDa poly-L-arginine hydrochloride (NP121).

Additionally, the peptides are well suited to formulation as sustained release dosage forms and the like. The formulations can be so constituted that they release the active peptide, for example, in a particular part of the intestinal or respiratory tract, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g. stents, catheters, peritoneal dialysis tubing, draining devices and the like.

For topical administration, the active agents may be formulated as is known in the art for direct application to a target area. Forms chiefly conditioned for topical application take the form, for example, of creams, milks, gels, powders, dispersion or microemulsions, lotions thickened to a greater or lesser extent, impregnated pads, ointments or sticks, aerosol formulations (e.g. sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic peptides of the invention can be delivered via patches or bandages for dermal administration. Alternatively, the peptide can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Pharmaceutical formulations for topical administration may comprise, for example, a physiologically acceptable buffered saline solution containing between about 0.001 mg/ml and about 100 mg/ml, for example between 0.1 mg/ml and 10 mg/ml, of one or more of the peptides of the present invention specific for the indication or disease to be treated.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active peptides can also be delivered via iontophoresis, e.g., as disclosed in U.S. Pat. Nos. 4,140,122; 4,383,529; or 4,051,842 which are incorporated herein by reference. The percentage by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the therapeutic peptides in an aqueous or non-aqueous base also comprising one or more dispersing agents, solubilizing agents or suspending agents. Liquid sprays can be pumped, or are conveniently delivered from pressurized packs. Drops can be delivered via a simple eye dropper-capped bottle, via a plastic bottle adapted to deliver liquid contents drop-wise, or via a specially shaped closure.

The therapeutic peptide may further be formulated for topical administration in the mouth or throat. For example, the active ingredients may be formulated as a lozenge further comprising a flavoured base, usually sucrose and acacia or tragacanth; pastilles comprising the composition in an inert base such as gelatine and glycerine or sucrose and acacia; and mouthwashes comprising the composition of the present invention in a suitable liquid carrier.

The peptides of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific infection, indication or disease. Any statistically significant attenuation of one or more symptoms of an infection, indication or disease that has been treated pursuant to the method of the present invention is considered to be a treatment of such infection, indication or disease within the scope of the invention.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g. gelatine or blister packs from which the powder may be administered with the aid of an inhalator, insufflator, or a metered-dose inhaler (see, for example, the pressurized metered dose inhaler (MDI) and the dry powder inhaler disclosed in Newinan, S. P. in Aerosols and the Lung, Clarke, S. W. and Davia, D. eds., pp. 197-224, Butterworths, London, England, 1984).

Therapeutic peptides of the present invention can also be administered in an aqueous solution when administered in an aerosol or inhaled form. Thus, other aerosol pharmaceutical formulations may comprise, for example, a physiologically acceptable buffered saline solution containing between about 0.001 mg/ml and about 100 mg/ml of one or more of the peptides of the present invention specific for the indication or disease to be treated. Dry aerosol in the form of finely divided solid peptide or nucleic acid particles that are not dissolved or suspended in a liquid are also useful in the practice of the present invention. Peptides of the present invention may be formulated as dusting powders and comprise finely divided particles having an average particle size of between about 1 and 5 µm, alternatively between 2 and 3 µm. Finely divided particles may be prepared by pulverization and screen filtration using techniques well-known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating the particular infection, indication or disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic peptides of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627 which are incorporated herein by reference. Aerosol delivery systems of the type disclosed herein are available from numerous commercial sources including Fisons Corporation (Bedford, Mass.), Schering Corp. (Kenilworth, N.J.) and American Pharmoseal Co. (Valencia, Calif.). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker).

Furthermore, the active ingredients may also be used in combination with other therapeutic agents, for example, pain relievers, anti-inflammatory agents, antihistamines, bronchodilators and the like, whether for the conditions described or some other condition.

Antimicrobial Use

According to a further aspect of the present invention there is provided a peptide as described above for use in therapy or prophylaxis.

According to a further aspect of the present invention there is provided a peptide as described above for use in the treating or preventing an antimicrobial infection or condition. Generally the peptide of the present invention is packaged and presented for use in treating or preventing an antimicrobial infection or condition.

According to a further aspect of the present invention, there is provided a method of treatment or prevention of an antimicrobial infection or condition comprising the step of administering a peptide of the present invention to a patient in need thereof.

The peptides of the invention are useful, inter alia, as antimicrobial peptides, for example, against bacteria, fungi, yeast, parasites, protozoa and viruses. The term, "antimicrobial peptide" can be used herein to define any peptide that has microbicidal and/or microbistatic activity and encompasses, non-exclusively, any peptide described as having anti-bacterial, anti-fungal, anti-mycotic, anti-parasitic, anti-protozoal, anti-viral, anti-infectious, anti-infective and/or germicidal, algicidal, amoebicidal, microbicidal, bacterici(o)dal, fungicidal, parasiticidal, protozoacidal, protozoicidal properties.

By "microbial infection" is meant an infection caused by a bacterial, parasitic, protozoan, viral or fungal pathogen. A "pathogen" is generally defined as any disease-causing organism.

In particular, the peptides of the present invention are useful as antibacterial peptides.

Thus, the invention further provides a peptide according to the invention for use as a medicament. The peptides of the invention may have application as antimicrobial agents both in vivo, in vitro and ex vivo.

A bacterial pathogen may be derived from a bacterial species selected from the group consisting of: *Staphylococcus* spp., e.g. *Staphylococcus aureus, Staphylococcus epidermidis; Enterococcus* spp., e.g. *Enterococcus faecalis, Enterococcus faecium; Streptococcus pyogenes; Listeria* spp.; *Pseudomonas* spp. e.g. *Pseudomonas aeruginosa; Mycobacterium* spp., e.g. *Mycobacterium tuberculosis; Enterobacter* spp.; *Klebsiella* spp., e.g. *Klebsiella pneumonia; Campylobacter* spp.; *Salmonella* spp.; *Streptococcus* spp., e.g. *Streptococcus* Group A or B, *Streptoccocus pneumoniae; Stenotrophomonas* spp., *Stenotrophomonas maltophilia; Helicobacter* spp., e.g. *Helicobacter pylori; Neisseria* spp., e.g. *Neisseria gonorrhea, Neisseria meningitidis; Borrelia burgdorferi; Shigella* spp., e.g. *Shigella flexneri; Escherichia coli; Haemophilus* spp., e.g. *Haemophilus influenzae; Chlamydia* spp., e.g. *Chlamydia trachomatis, Chlamydia pneumoniae, Chlamydia psittaci; Francisella fularensis; Bacillus* spp., e.g. *Bacillus anthracis; Clostridia* spp., e.g. *Clostridium botulinum, Clostridium perfringens, Clostridium difficile; Yersinia* spp., e.g. *Yersinia pestis; Treponema* spp.; *Burkholderia* spp.; e.g. *Burkholderia mallei, B. cepacia, B. cepacia* complex and *B. pseudomallei, Acinetobacter* spp. e.g. *A. baumanii* and *A. calcoaceticus; Achromobacter* spp., *Achromobacter xylosoxidans.*

The bacterial pathogen may be Gram-negative bacterium or a Gram-positive bacterium. The Gram-negative bacterium may be selected from the group consisting of *Pseudomonas* spp. (in particular *Pseudomonas aeruginosa*); *Burkholderia* spp (in particular *Burkholderia cepacia*); *Acinetobacter* spp. e.g. *A. baumanii* and *A. calcoaceticus; Streptococcus* spp., e.g. *Streptococcus* Group A or B, *Streptoccocus pneumoniae; Stenotrophomonas* spp., *Stenotrophomonas maltophilia* and *Achromobacter* spp., e.g. *Achromobacter xylosoxidans.*

The Gram-positive bacterium may be selected from the group consisting of *Staphylococcus* spp. (in particular *Staphylococcus aureus* and *Staphylococcus epidermidis*); *Escherichia coli; Clostridia* spp., e.g. *Clostridium botulinum, Clostridium perfringens, Clostridium difficile;* and *Enterococcus* spp., e.g. *Enterococcus faecalis, Enterococcus faecium.*

The bacterial pathogen may be selected from the group consisting of *Staphylococcus* spp. (in particular *Staphylococcus aureus* and *Staphylococcus epidermidis*); *Pseudomonas* spp. (in particular *Pseudomonas aeruginosa*); *Burkholderia* spp (in particular *Burkholderia cepacia*), *Escherichia coli; Acinetobacter* spp. e.g. *A. baumanii* and *A. calcoaceticus; Clostridia* spp., e.g. *Clostridium botulinum, Clostridium perfringens, Clostridium difficile; Enterococcus* spp., e.g. *Enterococcus faecalis, Enterococcus faecium; Streptococcus* spp., e.g. *Streptococcus* Group A or B, *Streptoccocus pneumoniae; Stenotrophomonas* spp., *Stenotrophomonas maltophilia* and *Achromobacter* spp., *Achromobacter xylosoxidans.*

The bacterial pathogen may be selected from the group consisting of *Staphylococcus* spp. (in particular *Staphylococcus aureus* and *Staphylococcus epidermidis*) and *Pseudomonas* spp. (in particular *Pseudomonas aeruginosa*).

The antimicrobial disease or condition/infection may be selected from the group consisting of boils, furuncles, cellulitis, impetigo, nosocomial infections, bacteraemia, pneumonia, osteomyelitis, endocarditis, meningitis, abscesses, cystic fibrosis (in particular lung infections in patients with cystic fibrosis), gastrointestinal infections, genitourinary infections, septicemia, pharyngitis, necrotizing fasciitis, acute glomerulonephritis, otitis media, wounds, anthrax, encephalitis, diphtheria, gas gangrene, botulism and tetanus.

Alternatively, the peptides of the present invention may be used to treat or alleviate a disease or condition selected from the group consisting of gonorrhea, meningitis, pneumonia, otitis media, osteomyelitis, cystic fibrosis (in particular lung infections in patients with cystic fibrosis), genitourinary infections, peritonitis, conjunctivitis, septicaemia, venereal disease, bacteremia, nosocomial infections, dysentery, gastrointestinal infections, typhoid fever, pneumonic plague, wounds, cholera, kidney infections, meliodiosis, conjunctivitis, pertussis, tularemia, brucellosis, Legionnaire's disease, peptic ulcer disease, typhus, pharyngitis.

The disease or condition to be treated may be contributed to or caused by an opportunistic bacterial infection, including diseases or conditions selected from the group consisting of urinary tract infections, respiratory tract infections, dermatitis, soft tissue infections, bacteremia, bone and joint infections, gastrointestinal infections and systemic bacterial infections in patients with severe burns, cancer, cystic fibrosis or AIDS.

The peptides of the present invention may have a minimum inhibitory concentration (MIC) of 32 µg/ml or less against Gram positive microbial pathogens, in particular bacterial pathogens. Generally the peptides have an MIC of 20 µg/ml or less, typically 16 µg/ml or less, suitably 10 µ/ml or less against Gram positive microbial pathogens. Advantageously, the peptides of the present invention have an MIC of around 8 µg/ml against Gram positive microbial pathogens, in particular Gram positive bacterial pathogens.

The peptides of the present invention may have a minimum inhibitory concentration (MIC) of 70 µg/ml or less against Gram negative microbial pathogens, in particular bacterial pathogens. Generally the peptides have an MIC of 50 µg/ml or less, typically 40 µg/ml or less, suitably 30 µg/ml or less against Gram negative microbial pathogens. Advantageously, the peptides of the present invention have an MIC of less than 30 µg/ml against Gram negative microbial pathogens, in particular Gram negative bacterial pathogens.

The MIC is generally measured at a pH of around 7.

The peptides of the present invention may have a minimum bactericidal concentration (MBC) of 250 µ/ml or less against Gram negative and Gram positive bacterial pathogens. Generally the peptides have an MIC of 125 µg/ml or less, typically 100 µg/ml or less, suitably 60 µg/ml or less against Gram negative and Gram positive bacterial pathogens. Advantageously, the peptides of the present invention have an MIC of less than 40 µg/ml against Gram negative and Gram positive bacterial pathogens.

A viral pathogen may be derived from a virus selected from the group consisting of: Human Immunodeficiency Virus (HTV1 & 2); Human T Cell Leukaemia Virus (HTLV 1 & 2); Ebola virus; human papilloma virus (e.g. HPV-2, HPV-5, HPV-8 HPV-16, HPV-18, HPV-31, HPV-33, HPV-52, HPV-54 and HPV-56); papovavirus; rhinovirus; poliovirus; herpesvirus; adenovirus; Epstein Barr virus; Influenza virus, hepatitis B and C viruses, Variola virus, rotavirus or SARS coronavirus.

A parasitic pathogen may be derived from a parasitic pathogen selected from the group consisting of *Trypanosoma* spp. (*Trypanosoma cruzi, Trypansosoma brucei*), *Leishmania* spp., *Giardia* spp., *Trichomonas* spp., *Entamoeba* spp., *Naegleria* spp., *Acanthamoeba* spp., *Schistosoma* spp., *Plasmodium* spp., *Crytosporidium* spp., *Isospora* spp., *Balantidium* spp., *Loa Loa*, *Ascaris lumbricoides, Dirofilaria immitis, Toxoplasma* ssp., e.g. *Toxoplasma gondii*. A fungal pathogen may be derived from a fungal pathogen which is of the genus *Candida* spp., (e.g. *C. albicans*), *Epidermophyton* spp., *Exophiala* spp., *Microsporum* spp., *Trichophyton* spp., (e.g. *T. rubrum* and *T. interdigitale*), *Tinea* spp., *Aspergillus* spp., *Blastomyces* spp., *Blastoschizomyces* spp., *Coccidioides* spp., *Cryptococcus* spp., *Histoplasma* spp., *Paracoccidiomyces* spp., *Sporothrix* spp., *Absidia* spp., *Cladophialophora* spp., *Fonsecaea* spp., *Phialophora* spp., *Lacazia* spp., *Arthrographis* spp., *Acremonium* spp., *Actinomadura* spp., *Apophysomyces* spp., *Emmonsia* spp., *Basidiobolus* spp., *Beauveria* spp., *Chrysosporium* spp., *Conidiobolus* spp., *Cunninghamella* spp., *Fusarium* spp., *Geotrichum* spp., *Graphium* spp., *Leptosphaeria* spp., *Malassezia* spp., *Mucor* spp., *Neotestudina* spp., *Nocardia* spp., *Nocardiopsis* spp., *Paecilomyces* spp., *Phoma* spp., *Piedraia* spp., *Pneumocystis* spp., *Pseudallescheria* spp., *Pyrenochaeta* spp., *Rhizomucor* spp., *Rhizopus* spp., *Rhodotorula* spp., *Saccharomyces* spp., *Scedosporium* spp., *Scopulariopsis* spp., *Sporobolomyces* spp., *Syncephalastrum* spp., *Trichoderma* spp., *Trichosporon* spp., *Ulocladium* spp., *Ustilago* spp., *Verticillium* spp., *Wangiella* spp.

The microbial infection may be a systemic, topical, subcutaneous, cutaneous or mucosal fungal infection.

Fungal infections can be classified as systemic, meaning that the infection is deep and affects internal organs or blood borne or topical (dermatophytic), meaning that the infection is superficial and occurs on the skin. Additionally, yeast infections can affect the mucous membranes of the body. Yeast infections can also be systemic (e.g. candidaemia and other frequently fatal conditions). Fungal infections on the skin are usually treated with creams or ointments (topical antifungal drugs). However, systemic infections, yeast infections or topical infections that do not clear up after treatment with creams or ointments may need to be treated with systemic antifungal drugs (oral or IV). These drugs are used, for example, to treat common fungal infections such as tinea (ringworm), which occurs on the skin or candidiasis (a yeast infection, also known as thrush), which can occur in the throat, in the vagina, or in other parts of the body. Systemic antifungal drugs are also used to treat other deep fungal infections such as histoplasmosis, blastomycosis, and aspergillosis, which can affect the lungs and other organs. They are sometimes used to prevent or treat fungal infections in people whose immune systems are weakened, such as bone marrow or organ transplant patients and people with HIV-AIDS.

Topical or dermatophyte fungal infections, while not typically causative of death or of serious illness, are prevalent and are economically important because they can be expensive to treat. Topical or superficial fungal infections may include those of the skin, lamina, stratum corneum, nails and hair. Cutaneous infections are infections of the skin, finger nails and toenails.

In a preferred aspect of the invention, the fungal infection is onychomycosis. Onychomycosis may be caused by a fungus from, but not limited to, the genus *Trichophyton* spp., for example, the fungus may be *Trichophyton interdigitale* or *Trichophyton rubrum*.

The term "onychomycosis" includes, but is not limited to, distal lateral subungual, superficial white, proximal white subungual, secondary dystrophic, primary dystrophic, endonyx, candidal (e.g. onycholysis & chronic mucocutaneous disease) types of onychomycosis. Onychomycosis has been shown as a significant risk factor for more serious clinical complications, such as acute bacterial cellulitis of the arm/leg and other secondary bacterial infections, thus the present invention encompasses the treatment of these infections.

The term "treatment" relates to the effects of the peptides described herein that in imparting a benefit to patients afflicted with an (infectious) disease, including an improvement in the condition of the patient or delay in disease progression.

The peptides of the invention, including their salts, are administered so as to achieve a reduction in at least one symptom associated with an infection, indication or disease, or a decrease in the amount of antibody associated with the indication or disease.

The peptides of the invention may also be useful in the treatment or prevention of, inter alia, wounds, ulcers and lesions for example, cutaneous wounds such cuts or burns, and conditions associated therewith.

The term "treatment" relates to the effects of the peptides described herein that in imparting a benefit to patients afflicted with an (infectious) disease, including an improvement in the condition of the patient or delay in disease progression.

As used herein "treatment of a wound" may include wound healing and associated conditions and therapy which promotes, augments, or accelerates healing of tissues and includes post-operative scarring, burns, psoriasis, acceleration of tissue remodelling, for example, post cosmetic surgery and organ transplantation.

Thus, in a further aspect of the invention there is provided a substrate to which a peptide of the invention is applied or attached. Preferably, the substrate is suitable for application to wounds or delivery to wound sites. Preferably, the substrate allows for the transfer of the peptides of the invention from the substrate to a wound bed to achieve their antibiotic effect. The substrate may be a dressing, for example, wound dressing. The dressing may comprise a fabric material or it may be a collagen-like material.

The peptides of the invention may also find application as/in a disinfectant, in this context, the peptide or pharmaceutical compositions of the invention may be applied, either alone or in combination with other disinfecting agents, to a surface to be treated. As used herein a "surface to be treated" may be a substrate as defined herein or a medical device. In a further aspect, the invention provides a method of treating or preventing a microbial infection in a subject comprising administering to said subject a therapeutically effective amount of a peptide according to the invention.

Mammals, birds and other animals may be treated by the peptides, compositions or methods described herein. Such mammals and birds include humans, dogs, cats and livestock, such as horses, cattle, sheep, goats, chickens and turkeys and the like. Moreover, plants may also be treated by the peptides, compositions or methods of the invention.

Where the subject is an animal, the peptides of the invention may be administered topically or systemically. In particular, peptides may be applied to the flesh of the animal or to nail-like features, including, but not exclusive to, hooves, claws and trotters.

The peptides of the present invention are generally non-toxic, and are generally well tolerated by mammals, birds, animals and plants. Typically the peptides of the present invention are well tolerated at doses of 2 to 10 mg/kg or more, suitably 2 to 6 mg/kg. For instance, peptide NP432 was found to be non-lethal to mice at a dose of around 5 mg/kg.

To achieve the desired effect(s), the peptide, a variant thereof or a combination thereof, may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight or at least about 1 mg/kg to about 20 mg/kg of body weight, although other dosages may provide beneficial results. The amount administered will vary depending on various factors including, but not limited to, the peptide chosen and its clinical effects, the disease, the weight, the physical-condition, the health, the age of the mammal, whether prevention or treatment is to be achieved, and if the peptide is chemically modified. Such factors can be readily determined by the clinician examining the empirical data from the clinical trials and examining the preclinical animal model results or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the peptides of the invention may be essentially continuous over a pre-selected period of time or may be in a series of spaced doses. Both local and systemic administration is contemplated.

To prepare the composition, peptides are synthesized or otherwise obtained, purified as necessary or desired, and then generally lyophilized and stabilized. The peptide can then be adjusted to the appropriate concentration and optionally combined with other agents. The absolute weight of a given peptide included in a unit dose can vary widely. For example, about 0.01 to about 2 g or about 0.01 to about 500 mg, of at least one peptide of the invention, or a plurality of peptides specific for a particular cell type can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the peptides of the invention can vary as well. Such daily doses can range, for example, from about 0.001 g/day to about 100 or 50 g/day, from about 0.1 g/day to about 25 g/day, from about 0.1 g/day to about 12 g/day, from about 0.1 g/day to about 5 g/day, from about 0.1 g/day to about 2.5 g/day, from about 0.1 g/day to about 2 g/day, from about 0.5 g/day to about 8 g/day, from about 0.5 g/day to about 4 g/day, from about 0.5 g/day to about 2 g/day, and from about 0.5 g/day to about 1 g/day.

Synergistic Effect

Preferably the composition includes one or more antimicrobial agents which act synergistically with the peptides of the present invention. Typically, the synergistic effect results in an increased antimicrobial effect. Generally the combined agents are associated with antimicrobial properties at least 10% greater than the additive antimicrobial properties of the two or more agents; typically at least 20% greater; suitably at least 30% greater; advantageously at least 50% greater than the additive antimicrobial properties of the two or more agents.

Generally the antimicrobial agent is an antibacterial agent and the composition exhibits a synergistically high antibacterial effect.

The synergistically high antibacterial effect may be evident with respect to and one of the group consisting of: *Staphylococcus* spp., e.g. *Staphylococcus aureus, Staphylococcus epidermidis; Enterococcus* spp., e.g. *Enterococcus faecalis, Enterococcus faecium; Streptococcus pyogenes; Listeria* spp.; *Pseudomonas* spp. e.g. *Pseudomonas aeruginosa; Mycobacterium* spp., e.g. *Mycobacterium tuberculosis; Enterobacter* spp.; *Klebsiella* spp., e.g. *Klebsiella pneumonia; Campylobacter* spp.; *Salmonella* spp.; *Streptococcus* spp., e.g. *Streptococcus* Group A or B, *Streptoccocus pneumoniae; Stenotrophomonas* spp., *Stenotrophomonas maltophilia; Helicobacter* spp., e.g. *Helicobacter pylori; Neisseria* spp., e.g. *Neisseria gonorrhea, Neisseria meningitidis; Borrelia burgdorferi; Shigella* spp., e.g. *Shigella flexneri; Escherichia coli; Haemophilus* spp., e.g. *Haemophilus influenzae; Chlamydia* spp., e.g. *Chlamydia trachomatis, Chlamydia pneumoniae, Chlamydia psittaci; Francisella fularensis; Bacillus* spp., e.g. *Bacillus anthracis; Clostridia* spp., e.g. *Clostridium botulinum, Clostridium perfringens, Clostridium difficile; Yersinia* spp., e.g. *Yersinia pestis; Treponema* spp.; *Burkholderia* spp.; e.g. *Burkholderia mallei, B. cepacia, B. cepacia* complex and *B. pseudomallei, Acinetobacter* spp. e.g. *A. baumanii* and *A. calcoaceticus; Achromobacter* spp., *Achromobacter xylosoxidans*.

The synergistic effect may be particularly evident with respect to *P. aeruginosa, S. epidermidis* and *S. aureus* bacteria; including against bacterial biofilms comprising such bacterial pathogens.

Alternatively, the synergistic effect may be evident due to a surprisingly low toxicity being associated with the combined agents. Generally the combined agents are associated with a toxicity at least 10% less than the additive associated toxicity of the two or more agents; typically at least 20% less; suitably at least 30% less; advantageously at least 50% less than the additive associated toxicity of the two or more agents.

A synergistic effect may be exhibited through a combination of one or more of the peptides of the present invention and one or more other antibacterial peptides.

According to one embodiment, the antibacterial peptides may be according to the Formula below:

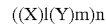

wherein l and m are integers from 1 to 10, for example 0 to 5; n is an integer from 1 to 10; X and Y, which may be the same or different, are an amino acid selected from the group consisting of hydrophobic amino acids and/or cationic amino acids. In a preferred aspect of the invention, the antibacterial peptide comprises from 3 to 200 amino acids, for example 3, 4, 5, 6 or 7 up to 100 amino acids, including 3, 4, 5, 6, or 7 up to 20, 25, 30, 35, 40 or 42 amino acids. The antibacterial peptide may comprise 100 to 200 amino acids, 27 to 100 amino acids, 28 to 86 amino acids, 7 to 27 amino acids or 3 to 14 amino acids. Typically the antibacterial peptide comprises 3 to 15 amino acids (for example 13 to 15), for example 3 to 7 amino acids. X and Y may be selected from phenylalanine and arginine. X may be a phenylalanine amino acid and Y may be an arginine amino acid.

According to one embodiment, there is provided a synergistic composition including a peptide comprising an amino acid sequence selected from the group RRRFRFFFRFRRR (SEQ ID NO: 1), HHHFRFFFRFRRR (SEQ ID NO: 2), KKFPWRLRLRYGRR (SEQ ID NO: 3), RRRRRFFFRFRRR (SEQ ID NO: 4), RRRFRFRFRFRRR (SEQ ID NO: 5), RRRFRFPFRFRRR (SEQ ID NO: 6), RRFRRFFFRRFRR (SEQ ID NO: 7), RRRRFFFRRRR (SEQ ID NO: 8), RRRRFRFRRRR (SEQ ID NO: 9), RRRRFPFRRRR (SEQ ID NO: 10), RRFRRRFRRFR (SEQ ID NO: 11), RRFRRRFRRFG (SEQ ID NO: 12), RRFGRRFRRFG (SEQ ID NO: 13), RRFRRFRRRFG (SEQ ID NO: 14), RRFRRFRRRFR (SEQ ID NO: 15), FRRRRFFFRFRRR (SEQ ID NO: 16), RRRRRFFFRRRRF (SEQ ID NO: 17), FFFFRRRRRFRRR (SEQ ID NO: 18), RRRRFFFFFRRRR (SEQ ID NO: 19), FRRRRFFFRRRRF (SEQ ID NO: 20), RRRYRYYYRYRRR (SEQ ID NO: 21), RRRARAAARARRR (SEQ ID NO: 22), RRRFRRRRRFFFF (SEQ ID NO: 23), RRRFFFFFFRRR (SEQ ID NO: 24) and RRRFRFFFRFRRR (SEQ ID NO: 25)-cysteamine together with one or more of cysteamine (NM001), polyarginine and polylysine, such as 10 to 20 kDa poly-L-lysine hydrobromide (NP108).

According to one embodiment, the composition comprises one of RRRFRFFFRFRRR (SEQ ID NO: 1) (NP432), RRRRRFFFRFRRR (SEQ ID NO: 4) (NP 465), RRRFRFRFRFRRR (SEQ ID NO: 5) (NP 466) and RRRFRFPFRFRRR (SEQ ID NO: 6) (NP 467) and one of cysteamine and polylysine, such as 10 to 20 kDa poly-L-lysine hydrobromide (NP108).

According to one embodiment, the composition comprises one of RRRFRFFFRFRRR (SEQ ID NO: 1) (NP432), FRRRRFFFRFRRR (SEQ ID NO: 16) (NP490), RRRRFFFFFRRRR (SEQ ID NO: 19) (NP493) and RRRFRRRRRFFFF (SEQ ID NO: 23) (NP497) and one of cysteamine and polylysine, such as 10 to 20 kDa poly-L-lysine hydrobromide (NP 108).

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Figure 6:
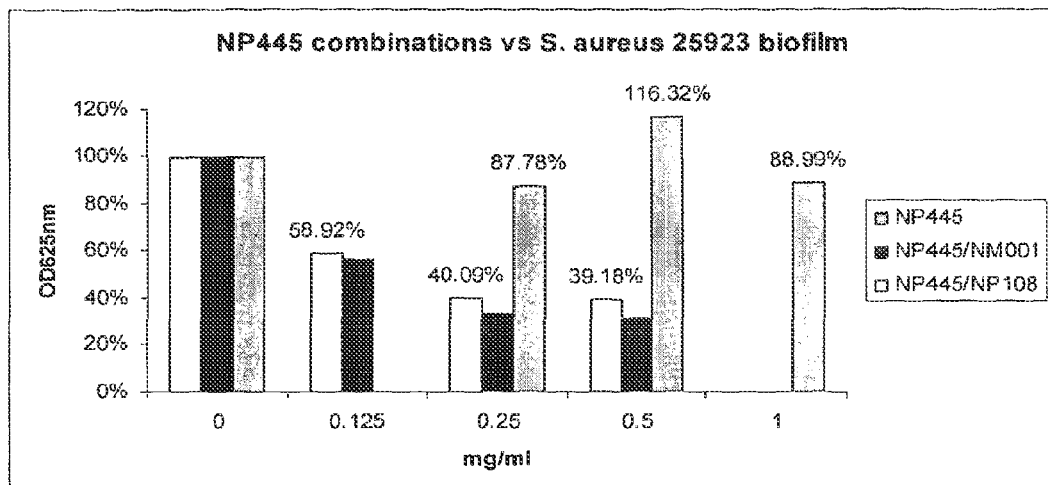
Figure 7:
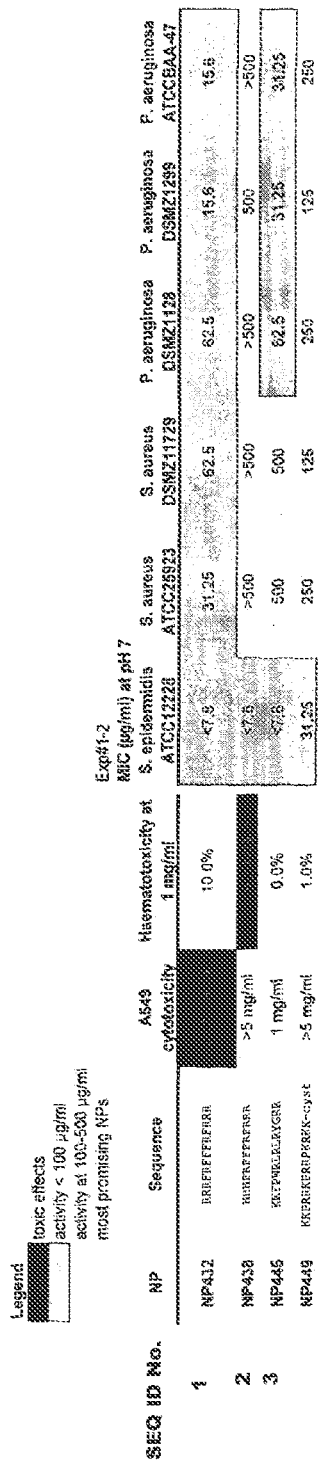
Figure 8:
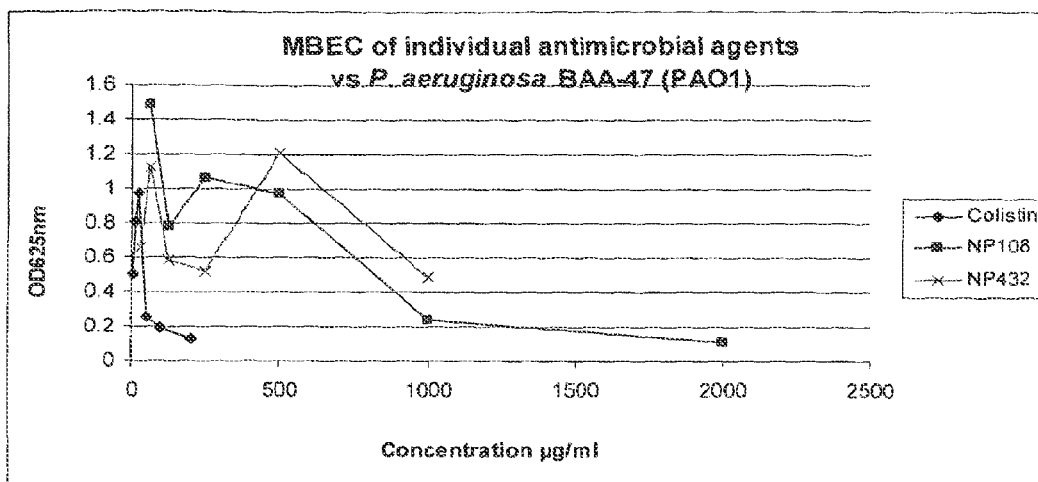
Figure 9:
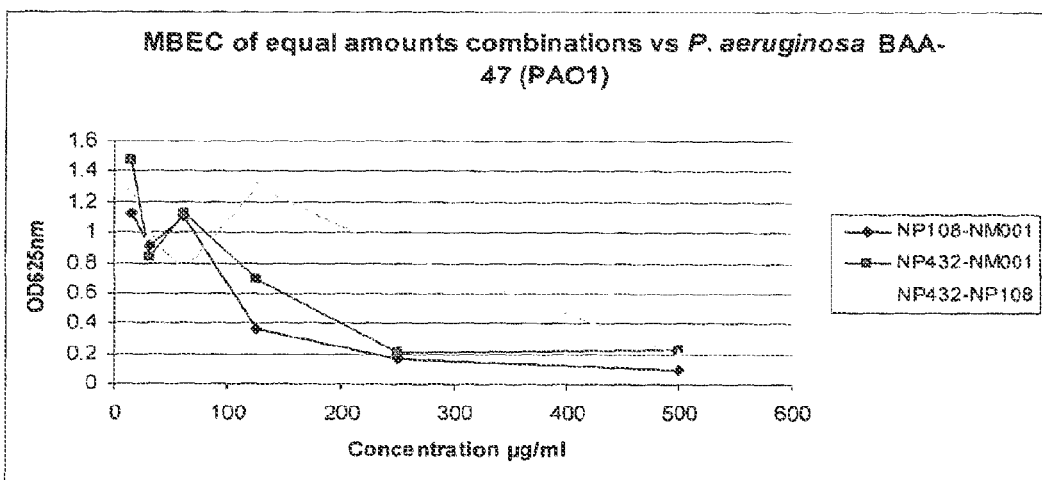
Figure 10:
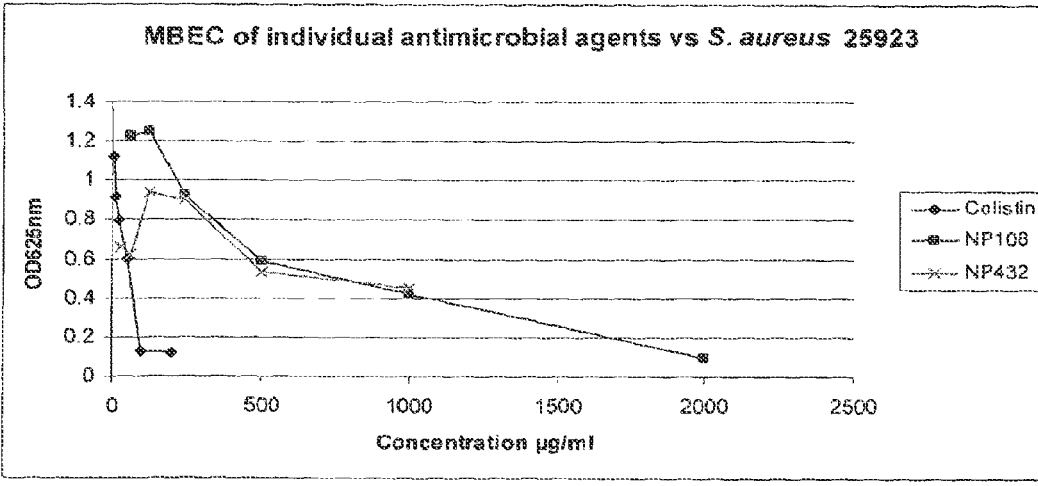
Figure 11:
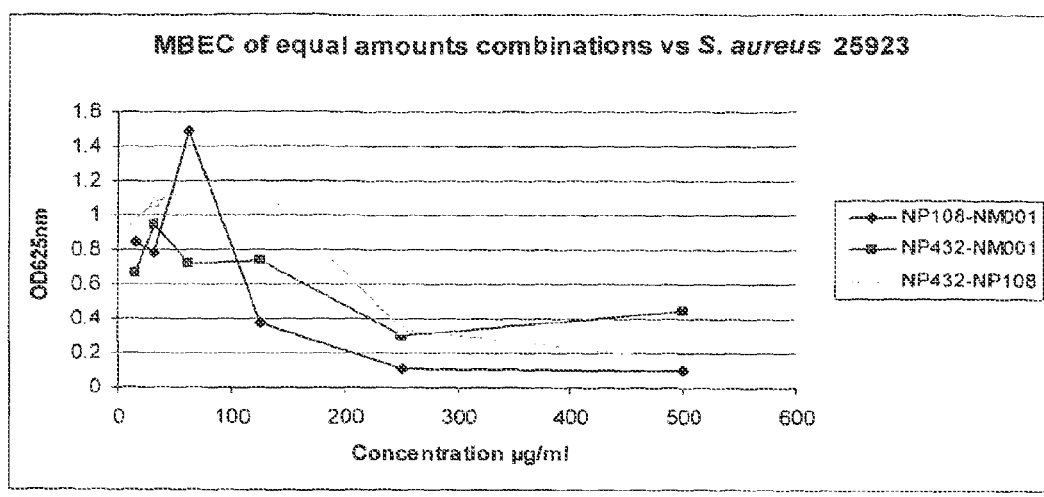

The present invention will now be described by way of example only with reference to the accompanying Figures in which:

FIG. 1 (SEQ ID Nos. 1-24) provides a table detailing the minimum inhibitory concentration (MIC) and minimum bactericidal concentration (MBC) of peptides according to the present invention against various Gram positive bacterial species (FIG. 1) and Gram negative bacterial species (FIGS. 1a (SEQ ID Nos. 1-24), 1b (SEQ ID Nos. 1-24) and 1c (SEQ ID Nos. 1-24));

FIG. 2 (SEQ ID Nos. 1-2 and 4-14) provides a table detailing the average minimum inhibitory concentration (MIC) of peptides according to the present invention against Gram + and Gram − microbial species;

FIG. 3 details the MIC of NP432, NP432 and NM001 and NP432 and NP 108 at varying concentrations against *P. aeruginosa* biofilm;

FIG. 4 details the MIC of NP445, NP445 and NM001 and NP445 and NP 108 at varying concentrations against *P. aeruginosa* biofilm;

FIG. 5 details the MIC of NP432 and NM001 and NP432 and NP 108 at varying concentrations against *S. aureus* biofilm;

FIG. 6 details the MIC of NP445, NP445 and NM001 and NP445 and NP 108 at varying concentrations against *S. aureus* biofilm FIG. 7 (SEQ ID Nos. 1-3) and FIG. 7a provides a table detailing the minimum inhibitory concentration (MIC) and minimum bactericidal concentration (MBC) of peptides according to the present invention against various antimicrobial species;

FIG. 8 details the MBEC of colistin, NP108 and NP432 at concentrations from 0 to 2500 μg/ml against *P. aeruginosa* bacterial biofilm;

FIG. 9 details the MBEC of combinations of NP108-NM001, NP432-NM001 and NP432-NP 108 against *P. aeruginosa* biofilm at concentrations of 0 to 600 μg/ml;

FIG. 10 details the MBEC of colistin, NP108 and NP432 at concentrations from 0 to 2500 μg/ml against *S. aureus* bacterial biofilm;

FIG. 11 details the MBEC of combinations of NP108-NM001, NP432-NM001 and NP432-NP108 against *S. aureus* biofilm at concentrations of 0 to 600 μg/ml.

EXAMPLES

Example 1

*P. aeruginosa* bacterial biofilms and *S. aureus* bacterial biofilms were grown in Mueller-Hinton agar in separate 96-well microtitre plates for 21 hours at 37 degrees Celsius. The planktonic cells and medium were then removed and the bacterial biofilms were washed three times with phosphate buffer solution at a pH of around 7. Two-fold dilutions of three different antimicrobial agents in Mueller Hinton broth were then added to the bacterial biofilms. The microtitre plates were incubated at 37 degrees Celsius for 24 hours. The medium was then transferred to a fresh microtitre plate and the optical density of the bacterial biofilm was measured at 625 nm on a microtitre plate reader (BioTek Powerwave, XS, Winooski, USA.

The antimicrobial agents tested were Colistin, NP108 and NP432. Firstly, the activity of the antimicrobial agents at concentrations from 0 to 2500 μg/ml was tested, then the activity of the antimicrobial agents at concentrations from 0 to 600 μg/ml was tested. The results are summarised in FIGS. 8 to 11. These figures evidence the antimicrobial effect of a peptide of the present invention (NP432) against *P. aeruginosa* bacterial biofilms and against *S. aureus* bacterial biofilm. The antimicrobial effect is comparative to known antimicrobial agents.

Example 2

*P. aeruginosa* bacterial biofilms and *S. aureus* bacterial biofilms were grown in Mueller-Hinton agar in separate 96-well microtitre plates for 18 hours at 37 degrees Celsius.

The planktonic cells and medium were then removed and the bacterial biofilms were were washed three times with phosphate buffer solution at a pH of around 7. Two-fold dilutions of three different antimicrobial agents in Mueller Hinton broth were then added to the bacterial biofilms. The microtitre plates were incubated at 37 degrees Celsius for 24 hours. The medium was then transferred to a fresh microtitre plate and the optical density of the bacterial biofilm was measured at 625 nm on a microtitre plate reader (BioTek Powerwave, X S, Winooski, USA.

The antimicrobial agents tested were NP432 alone, a combination of NP432 and NM001 in equal concentration, a combination of NP432 and NP 108 in equal concentration, NP445 alone, a combination of NP445 and NM001 in equal concentration, a combination of NP445 and NP 108 in equal concentration. The antimicrobial agents were tested at concentrations of 0 to 1 mg/ml against *P. aeruginosa* bacterial biofilms and *S. aureus* bacterial biofilms. The results are summarised in FIGS. 3 to 6. These figures evidence the antimicrobial effect of a peptide of the present invention (NP432 and NP445) against *P. aeruginosa* bacterial biofilms and against *S. aureus* bacterial biofilm, alone and in combination with NM001 and NP108.

The invention claimed is:

1. A peptide consisting of amino acid sequence selected from the group RRRFRFFFRFRRR (SEQ ID NO: 1), HHHFRFFFRFRRR (SEQ ID NO: 2), KKFPWRLRLRYGRR (SEQ ID NO: 3), RRRRRFFFRFRRR (SEQ ID NO: 4), RRRFRFRFRFRRR (SEQ ID NO: 5), RRRFRFPFRFRRR (SEQ ID NO: 6), RRFRRFFFRRFRR (SEQ ID NO: 7), RRRRFFFRRRR (SEQ ID NO: 8), RRRRFRFRRRR (SEQ ID NO: 9), RRRRFPFRRRR (SEQ ID NO: 10), RRFRRRFPFRRFR (SEQ ID NO: 11), RRFRRRFRRFG (SEQ ID NO: 12), RRFGRRFRRFG (SEQ ID NO: 13), RRFRRFRRRFG (SEQ ID NO: 14), RRFRRFRRRFR (SEQ ID NO: 15), FRRRRFFFRFRRR (SEQ ID NO: 16), RRRRRFFFRRRRF (SEQ ID NO: 17), FFFFRRRRRFRRR (SEQ ID NO: 18), RRRRFFFFFRRRR (SEQ ID NO: 19), FRRRRFFFFRRRF (SEQ ID NO: 20), RRRYRYYYRYRRR (SEQ ID NO: 21), RRRARAAARARRR (SEQ ID NO: 22), RRRFRRRRRFFFF (SEQ ID NO: 23), and RRRFFFFFFFRRR (SEQ ID NO: 24).

2. A method for the treatment or delay of progression of a microbial infection wherein said infection is a bacterial infection which comprises administering to a patient a therapeutically effective amount of the peptide of claim 1, or a pharmaceutically acceptable salt thereof.

3. The method of claim 2 comprising administering the peptide, or pharmaceutically acceptable salt thereof via a route selected from: topical, oral, parenteral, subcutaneous, intravenous, intramuscular, intraperitoneal, rectal, dermal, transdermal, intrathoracic, intrapulmonary, mucosal, intranasal, and respiratory routes.

4. A composition comprising a pharmaceutically effective amount of at least one peptide of claim 1 and a pharmaceutically acceptable carrier, excipient or diluent.

5. A composition comprising a pharmaceutically effective amount of at least two peptides of claim 1 and a pharmaceutically acceptable carrier, excipient or diluent, wherein the peptides are different.

6. The composition of claim 4 further comprising cysteamine and/or polylysine.

7. A substrate to which is attached or applied a peptide of claim 1.

8. The method of claim 2 wherein the microbial infection is contributed to or caused by a bacterial pathogen.

9. The method of claim 8 wherein the bacterial pathogen is a Gram-negative bacterium.

10. The method of claim 9 wherein the Gram-negative bacterium is selected from the group consisting of *Pseudomonas* spp., *Burkholderia* spp., *Acinetobacter* spp., *Streptococcus* spp., *Stenotrophomonas* spp., and *Achromobacter* spp.

11. The method of claim 8 wherein the bacterial pathogen is a Gram-positive bacterium.

12. The method of claim 11 wherein the bacterial pathogen is a Gram-positive bacterium is selected from the group consisting of *Staphylococcus* spp., *Escherichia coli, Clostridia* spp., and *Enterococcus* spp.

13. The method of claim 8 wherein the bacterial pathogen is of the genus *Staphylococcus* spp or *Pseudomonas* spp.

14. The method of claim 8 wherein the microbial infection is selected from the group consisting of boils, furuncles, cellulitis, impetigo, nosocomial infections, bacteraemia, pneumonia, osteomyelitis, endocarditis, meningitis, abscesses, cystic fibrosis, gastrointestinal infections, genitourinary infections, septicemia, pharyngitis, necrotizing fasciitis, acute glomerulonephritis, otitis media, wounds, anthrax, encephalitis, diphtheria, gas gangrene, botulism and tetanus.

* * * * *